US006730047B2

(12) United States Patent
Socci et al.

(10) Patent No.: US 6,730,047 B2
(45) Date of Patent: May 4, 2004

(54) HEAD GEAR INCLUDING A DATA AUGMENTATION UNIT FOR DETECTING HEAD MOTION AND PROVIDING FEEDBACK RELATING TO THE HEAD MOTION

(75) Inventors: Roger David Socci, Reston, VA (US); Robert L Wakenight, New Market, MD (US); Mark Winthrop Wheeler, Groton, MA (US); Mark William Donahue, Maynard, MA (US); Olin Glenn Lathrop, Groton, MA (US); Robert Jonathan Schmidt, Harvard, MA (US)

(73) Assignee: Creative Sports Technologies, Inc., Woodbridge, VA (US)

( * ) Notice: Subject to any disclaimer, the term of this patent is extended or adjusted under 35 U.S.C. 154(b) by 0 days.

(21) Appl. No.: 09/784,080

(22) Filed: Feb. 16, 2001

(65) Prior Publication Data

US 2002/0183657 A1 Dec. 5, 2002

Related U.S. Application Data

(63) Continuation-in-part of application No. 09/521,102, filed on Mar. 7, 2000, now Pat. No. 6,331,168, which is a continuation-in-part of application No. 09/337,007, filed on Jun. 28, 1999, now Pat. No. 6,048,324, which is a continuation of application No. 08/957,073, filed on Oct. 24, 1997, now Pat. No. 5,916,181.

(51) Int. Cl.[7] .......................... A61B 5/103; A61B 5/117
(52) U.S. Cl. ...................................... 600/595
(58) Field of Search .................. 33/511, 512; 340/573; 473/209; 600/595, 587

(56) References Cited

U.S. PATENT DOCUMENTS

| 4,300,765 A | 11/1981 | Stringham |
| 4,326,303 A | 4/1982 | Rappleyea |
| 4,446,480 A | 5/1984 | Breglia et al. |

(List continued on next page.)

FOREIGN PATENT DOCUMENTS

JP  5-131040  5/1993

OTHER PUBLICATIONS

Electronic Baseball (Babe Ruth would die); Daniel Ruby; Jul. 1982, Popular Science, p. 63.

(List continued on next page.)

*Primary Examiner*—Max F. Hindenburg
*Assistant Examiner*—Jonathan Foreman
(74) *Attorney, Agent, or Firm*—Hunton & Williams LLP

(57) ABSTRACT

The invention disclosed includes a head gear to be worn when it is desirable to have an indication of the wearer's head motion or position. The head gear may be incorporated into an existing article of head wear. The incorporation may be permanent, or the head gear may be alternatively attached to various articles of head wear. Integral with the head gear are motion and/or position sensing devices to indicate the motion or position of the wearer's head. The data from the sensors may be fed into a digital processor to process the sensed data and derive a signal indicative of the wearer's head motion or position. Some embodiments employ a programmable processor to adapt the head gear to a variety of applications. The signal indicative of head motion or position may be fed into an indicator to provide the wearer with a recognizable feedback signal indicative of head motion or position.

49 Claims, 16 Drawing Sheets

U.S. PATENT DOCUMENTS

| | | | |
|---|---|---|---|
| 4,502,035 A | | 2/1985 | Obenauf et al. |
| 4,517,417 A | | 5/1985 | Murayama |
| 4,605,226 A | * | 8/1986 | Morrissey ................ 340/573.6 |
| 4,729,132 A | | 3/1988 | Fierro |
| 4,826,165 A | | 5/1989 | Socci |
| 4,869,509 A | | 9/1989 | Lee |
| 5,003,631 A | | 4/1991 | Richardson |
| 5,108,104 A | | 4/1992 | Johnson |
| 5,142,700 A | | 8/1992 | Reed |
| 5,221,088 A | | 6/1993 | McTeigue et al. |
| 5,251,902 A | | 10/1993 | Federowicz et al. |
| 5,287,562 A | | 2/1994 | Rush, III |
| 5,300,921 A | * | 4/1994 | Hoch et al. ................. 702/153 |
| 5,380,001 A | | 1/1995 | Socci et al. |
| 5,428,846 A | | 7/1995 | Socci et al. |
| 5,430,435 A | | 7/1995 | Hoch et al. |
| 5,524,894 A | | 6/1996 | Shannon |
| 5,538,250 A | | 7/1996 | Putz |
| 5,539,935 A | | 7/1996 | Rush, III |
| 5,546,609 A | | 8/1996 | Rush, III |
| 5,553,857 A | | 9/1996 | Fish |
| 5,558,585 A | | 9/1996 | Nolan, Jr. |
| 5,573,011 A | | 11/1996 | Felsing |
| 5,592,401 A | * | 1/1997 | Kramer ...................... 702/153 |
| 5,615,132 A | | 3/1997 | Horton et al. |
| 5,645,077 A | | 7/1997 | Foxlin |
| 5,713,804 A | | 2/1998 | Socci et al. |
| 5,916,181 A | | 6/1999 | Socci et al. |
| 5,978,972 A | * | 11/1999 | Stewart et al. ................. 2/422 |
| 6,048,324 A | | 4/2000 | Socci et al. |
| 2002/0151994 A1 | * | 10/2002 | Sisco .......................... 700/91 |
| 2003/0024311 A1 | * | 2/2003 | Perkins ........................ 73/493 |

OTHER PUBLICATIONS

Declaration In Support Of An Information Disclosure Statement, Roger Socci; Jan. 1998.

How to Perfect Your Golf Swing, Jimmy Ballard, Golf Digest Books, pp. 69–74.

The Eight Step Swing, Jim Mclean, Harper Collins, 1994, pp. 20–21, 25.

* cited by examiner

HEAD GEAR INCLUDING A DATA AUGMENTATION UNIT FOR DETECTING HEAD MOTION AND PROVIDING FEEDBACK RELATING TO THE HEAD MOTION

REFERENCE TO RELATED APPLICATIONS

This application is a continuation-in-part of application Ser. No. 09/521,102, filed, Mar. 7, 2000 now U.S. Pat. No. 6,331,168, which is a continuation-in-part of application Ser. No. 09/337,007, filed Jun. 28, 1999 now U.S. Pat. No. 6,048,324, which, in turn, is a continuation of application Ser. No. 08/957,073, filed Oct. 24, 1997, now U.S. Pat. No. 5,916,181.

FIELD OF THE INVENTION

The invention relates to a system and method for using head gear to sense a wearer's head motion during a physical activity and comparing the detected head motion to predetermined desirable head motion paths. In particular, the invention relates to a system and method for providing feedback to the head gear wearer to assist the wearer in achieving the desirable head motion.

BACKGROUND OF THE INVENTION

The ability to monitor the motion of a person's head has importance in many applications. For example, in many sports, the relative position and/or motion of a player's head is essential in executing a desired athletic movement. Typically, in order to achieve the correct head position or movement, the player must practice. Traditionally, such practice has encompassed repeating the position or movement until it is properly executed. A significant problem with this repetitive practice approach is the player must generally rely on self-inspection to determine whether the motion or position is correct. Endless hours of unknowingly practicing the incorrect motion will input improper data into the player's muscle memory or motor memory and will make it difficult for the player to achieve the intended improvement. A second party observer (e.g., a coach) can sometimes provide insight to correct the motion. However, this method depends upon the knowledge, communication skills and availability of such an expert observer. A video tape recorder can substitute for an observer. However, using a video recording requires the purchase of costly equipment and often the tape can only be viewed after the practice session has taken place. Thus, corrections can only be attempted at a subsequent practice session.

Monitoring head movement and relative position has numerous safety applications. For example, in those sports considered to be contact sports (e.g., football, hockey, lacrosse, etc.), a player making contact with his or her head in the wrong position risks injury. A warning signal would give the player an opportunity to alter his or her head position in time to avoid injury. Current head gear for these types of contact sports do not provide any sensor information to indicate a dangerous head position.

A head position monitor has safety applications in situations where head position indicates other dangerous conditions. For example, certain movements of an automobile driver's head indicate that the driver has fallen asleep at the wheel or is not looking at the road. Many accidents could be avoided if the driver is prompted to regain proper head position. Likewise, in aviation a pilot's head position in certain instances can create a potentially dangerous situation. For example, when an aircraft is in a turn and a pilot's head is positioned at an improper angle with respect to the vertical of the centerline of the aircraft, disorientation can occur. This may occur when the inner ear of a pilot provides an erroneous sense of turn information to the pilot while making a prolonged, constant bank turn such that the pilot may incorrectly believe that he or she has ceased turning and has leveled off. While many cockpits include attitude and altitude indicators to alert the pilot to the aircraft's attitude and altitude, current head gear for pilots do not provide a head position sensor indicating a dangerous, prolonged, constant banked turn. Providing an alarm alerting the pilot of improper head position can be a significant safety advantage in this circumstance.

Many drawbacks exist among current head position monitors. For example, many devices are not sensitive to small amplitude head motions, thus, these motions remain undetected. Another drawback of existing devices is that often the desired motion requires a deliberate, predetermined head motion and many existing devices are set to merely indicate when the head has moved. For example, to properly hit a baseball the batter's head should move to follow the pitch from the pitcher to the catcher. Existing head motion sensors that merely indicate when a batter's head moves are not useful to indicate the proper head motion to the batter. Another drawback is that many existing devices are bulky and cumbersome. To be practical, a head motion monitor should interfere with the wearer and activity as little as possible. Another drawback is that many existing devices are not adaptable to the skill level of the wearer. For example, it may be desirable for the sensitivity of a head motion detecting device for a professional baseball batter to be finer tuned than the sensitivity of a head motion detecting device for a little league baseball batter; many existing devices cannot adapt to these different sensitivity levels.

Many places offer personal training services during which a coach or other professional advisor observe and help to teach a player to execute proper head motion. For example, golf courses, tennis clubs, and baseball batting cages, often offer professional training. A drawback with professional lessons is that they are often expensive. In addition, for players without the time, money, or ability to travel, professional feedback is not easily attainable. These and other drawbacks exist in current devices.

SUMMARY OF THE INVENTION

An object of the invention is to overcome the above enumerated drawbacks and others present in existing devices.

Another object of the invention is to provide head gear that provides real time feedback to the wearer to aid the wearer in maintaining proper relative head position while participating in sports.

Another object of the invention is to provide head gear that detects the motion of the wearer's head about two mutually perpendicular axes.

Another object of the invention is to provide a very simple device to teach players the correct method for hitting a ball.

Another object of the invention is to provide head gear that relays safety information to the wearer regarding the wearer's head position.

Another object of the invention is to provide head gear with memory capable of storing data pertaining to desired motions.

Another object of the invention is to provide real time feedback to the wearer to aid the wearer in achieving proper head motion and related shoulder position during the course of a swing while participating in sports.

Another object of the invention is to provide real time feedback to pilots during a turn indicating a dangerous, prolonged, constant banked turn.

Another object of the invention is to provide head gear capable of alerting a driver of a potentially dangerous head position.

To accomplish these and other objects of the invention there is disclosed head gear to be worn when it is desirable to have an indication of the wearer's head motion or position. The head gear may be incorporated into an existing article of head wear. The incorporation may be permanent, or the head gear may be alternatively attached to various articles of head wear. Integral with the head gear are motion and/or position sensing devices to indicate the motion or position of the wearer's head. The data from the sensors may be fed into a digital processor to process the sensed data and derive a signal indicative of the wearer's head motion or position. Some embodiments employ a programmable processor to adapt the head gear to a variety of applications. The signal indicative of head motion or position may be fed into an indicator to provide the wearer with a recognizable feedback signal indicative of head motion or position.

Preferably, the head gear comprises a unitary construction that can be incorporated into existing head wear. The head gear is preferably of such a size and weight to be relatively unobtrusive to the wearer. Some embodiments of the head gear are attachable to more than one kind of existing head wear to enable use in multiple applications. Some embodiments of the head gear may be permanently incorporated into existing head wear.

Among other applications, the head gear allows the wearer to practice and perfect a desired motion. For example, applied to baseball, the head gear provides the wearer with feedback indicating the amount of head tilt and head turning or rotation that occurs during the act of swinging a bat at a pitch. The batter receives feedback during the swing, allowing the batter to immediately pinpoint the correct or incorrect head motion. Thus, the batter is provided with the information necessary to correct his or her head position for the next swing and does not have to rely on guess work. The batter receives the information instantaneously, he or she does not have to wait to view a video later, or after the practice session has ended. Furthermore, there is no need to acquire and rely on a second party observer. The head gear allows the wearer a simple and relatively inexpensive method and apparatus to practice.

When the head motion monitor is used in safety applications the operation is similar. The motion and/or position sensing devices indicate the motion or position of the wearer's head. The data from the sensors are fed into a processor to process the data and derive a signal indicative of the wearer's head motion or position. The processor is programmed to indicate when the wearers head is in an unsafe position and to output a signal to the indicator to notify the wearer of the unsafe condition. Thus, the head gear can be used to help reduce the risk of injury in many situations.

Another embodiment of the invention provides a multi-piece head gear assembly to monitor user head motion and provide feedback. For example, head motion sensors may be placed in a wearable head piece for the user to wear. In some embodiments, the head piece may contain head motion sensors; processing and other peripheral function may be housed n a separate portable unit. For example, the head piece may contain a number of gyroscopic sensors, accelerometer sensors, or a combination of both, to sense rotation and translation of the wearer's head during the physical movement.

The head piece may also include a mechanism to convey the sensor signals to the processor. Any suitable mechanism may be used to convey the sensor signals. For example, a cable, wire, or other connection may be provided between the wearable head piece and the processor, or a wireless transmitter/receiver combination may be used to convey signals between the head piece and the processor.

In some embodiments the processor may be housed in a portable data augmentation unit (DAU). The DAU may comprise any suitable portable processing device. For example, the DAU may comprise a dedicated head motion processing device specifically designed for the task, a palm sized processing device (e.g., Palm Pilot™, or other personal digital assistant (PDA)) with suitable software, a suitably equipped Web enabled cellular phone, or other processor based device.

In some embodiments, a DAU may be used to provide the wearer with feedback during the execution of the physical movement. For example, a DAU may comprise a visual display screen to display feedback messages, an audible feedback signal transmitter (e.g., a speaker or other audible signal transmitter), a mechanical vibrator to transmit vibratory feedback signals, or other suitable feedback signal transmitter.

In some embodiments, a DAU may be used to upload (i.e., transmit files or data to another processor based device) head gear data. For example, a DAU may upload stored swing data to a personal computer (PC) or other processor based device for further analysis using software on the PC.

In some embodiments, a DAU may upload head gear data to an interactive World Wide Web (Web) site. The data may be processed using software accessible at the Web site, or the data may be viewed and analyzed by a professional or coach with access to the web site. For example, a golfing embodiment of the head gear may be used to collect data pertaining to a golfer's head motion during a golf game. The golfer may store head gear information during the game and upload the stored data to Web site granting access to a golf instructor (e.g., an instructor from Jim Mclean's Golf School who analyzes the head gear data and provides feedback to the golfer via the Web site (e.g., in the golfer's Web site account), electronic mail (e-mail), or other suitable method.

Some embodiments of the invention may comprise a data collection unit (DCU) that functions as a diagnostic and research tool for the collection of body motion data. The DCU may interface with numerous sensors and processors to compile data used, for example, to create the processing routines for desired head motion for various physical activities. Other applications for the DCU will be apparent to those skilled in the art.

DETAILED DESCRIPTION OF THE DRAWINGS

Figure 1:
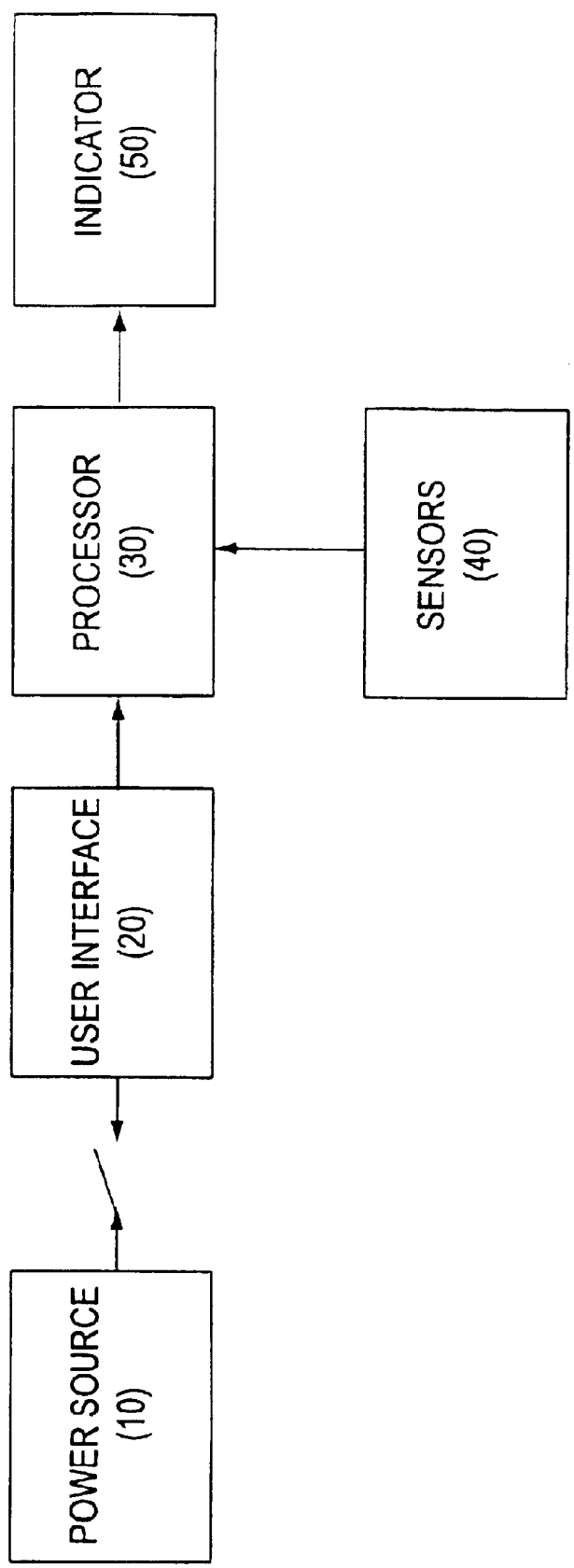
FIG. 1 is a schematic block diagram of an embodiment of the present invention.

The operation of the present invention to achieve the objects stated above will be better understood by reference to the drawings and detailed description below.

The head motion sensor head gear apparatus, to achieve the objects of the invention, may include five main functional blocks: power supply, processor, sensing mechanism, user interface, and an indicator. These functional elements operate to provide the benefits described above. Each block is discussed separately below. However, they operate together as indicated.

Power Supply

The power source 10 for the head gear preferably comprises a standard 9 Volt alkaline battery. These batteries are readily available in the retail market and are inexpensive. The 9 Volt battery has sufficient capacity to power the head gear for approximately 30 hours of continuous operation. More exotic batteries (e.g., Ni-Cad, etc.,), renewable batteries, rechargeable batteries or other suitable power sources are available. Other embodiments, having different power requirements may employ other power sources. For example, power sources supplying more or less than 9 V may be incorporated as desired.

Preferably, the 9 Volts from the battery may be regulated to the required 5 Volts by a linear voltage regulator. A protection device, such as a blocking diode, may be used to protect the regulator if the battery is inadvertently installed with the wrong polarity. A momentary switch can be used as the power on/off switch. This switch and associated circuitry apply power to processor 30 for a long enough time for processor 30 to "wake up" and latch the on condition of the head gear. In one embodiment, the head gear can be turned off in two different ways. First, the user can activate the momentary power switch to turn the head gear on or off. Second, the processor 30 can turn off the head gear on its own. For example, if the processor 30 has determined that the head gear has not been used for a preprogrammed period of time, the processor 30 will unlatch the power source 10 and go to "sleep." This feature conserves the available power source 10 capacity in those applications where power conservation is desirable.

Processor

Processor 30 is preferably a microprocessor chip, for example, the Microchip PIC16C72 or PIC16C73. This type of processor typically has 2–4 K bytes of on-chip program memory, 128–192 bytes of on-chip data memory, 3 timer modules, 5 analog to digital converter channels (8 bit resolution), a watchdog timer, power on reset circuitry, programmable I/O pins, and interrupt capabilities. These values are merely exemplary of the features desirable to provide a single chip solution to the processing requirements. The PIC16C73 also comprises a universal asynchronous receiver/transmitter (UART) to enable interfacing with a personal computer (or the like). This capability is advantageous for those embodiments where it is desired to perform data analysis or other diagnostics. Processor 30 may also comprise similar microprocessors chips made by other manufacturers.

The power on reset circuitry ensures that the processor is properly initialized when first turned on. The watchdog timer ensures that the program embedded in the processor is running properly. If the program should "crash," that is cease to function properly, the processor will automatically reset itself. For those embodiments of the head gear comprising two motion sensors, preferably, two channels of the analog to digital converter are used to convert the analog data from the two sensors into a digital form which can be analyzed by the embedded program in the processor. Preferably, two of the available timer modules are used in the head gear. One timer is, preferably, set to interrupt at a 60 Hz rate. This is the sample period for the analog to digital conversions and also provides a timer tick for various time-out periods in the operation of the head gear. The second timer is, preferably, programmed to interrupt on every half cycle of the selected frequency being applied to the indicator. Preferably, programmable I/O pins are used to read the user interface switches, to provide drive for the audible indicator, and to control the power supply latching circuitry.

For embodiments of the head gear equipped with the ability to store data in memory additional processor chips may be provided. For example, a static RAM chip may be incorporated into the head gear to enable the ability to store sensor data. Typically, the static RAM may operate with a processor such as an Intel 80C51 processor, or a similar device. Such a processor may be used instead of the above described PIC type microprocessor. A flash memory device may also be incorporated into embodiments where the speed of data storage is not an issue. Other types of memory storage chips may also be used.

Sensors

In some embodiments, the head gear preferably uses two sensors 40 and measures the angular motion of the wearer's head about two axes. One sensitive axis passes through the ears of the wearer and will be referred to as the X axis. The second sensitive axis passes out the top of the wearer's head and will be referred to as the Z axis. Other embodiments may comprise more sensors to detect motion about other axes. For example, sensors may be incorporated to detect motion along the Y axis, which can be envisioned as passing horizontally out through the tip of the wearer's nose. For embodiments where motion detection is only along one axis, fewer sensors may be used.

Rotation about the X axis is a measure of the tilting and turning of the wearer's head. In those embodiments of the head gear adapted to sports, it is important to monitor head tilt because, in many sports the degree and direction of a player's head tilt is indicative of the correctness of the motion. For example, in baseball, a batter's head should not tilt up during the swing and, in fact, should naturally tilt slightly downward. Likewise, in golf a player's head should not tilt up during a swing. Therefore, if the tilt of the head is up, the player is not watching the ball to the point at which the bat or club contacts the ball.

Rotation about the Z axis is a measure of the rotation of the wearer's head during the motion. For example, in many sports it is preferable for the player's head to follow the motion of the ball throughout the swing. For example, in baseball, a batter's head should initially rotate slightly, from the set position of the stance, toward the catcher. This indicates that the batter is actually tracking the baseball as it leaves the pitcher's hand and approaches home plate. The batter's head should stay in this position until some time after the baseball is contacted. Training the head to remain in position until some time after contact helps to ensure that the batter is getting proper separation of the head from the front shoulder during the swing. If the rotation of the batter's head is initially away from the catcher, the batter is not tracking the ball properly and is said to be "pulling off the ball." If the rotation away from the catcher occurs too quickly, the batter will not be getting the proper separation of head and front shoulder during the swing and the batter will not contact the ball properly. Similar head rotation analysis for other sports can also be accommodated by the head gear.

One embodiment of the head gear measures the angular motion around the two sensitive axes (e.g., X and Z) with two gyroscopes oriented such that each gyroscope is only sensitive to rotations about one of the axes. The outputs of the gyroscopes are, preferably, analog voltages proportional to the angular rate at which the gyroscope is moving about its axis of sensitivity. The gyroscopes are preferably mounted on head gear being worn by the player, therefore, the outputs of the gyroscopes are indicative of the angular motion of the wearer's head about the two sensitive axes. The data output of the gyroscopes is proportional to the speed of rotation and a simple mathematical manipulation of the data yields the position of the wearer's head. A single integration of speed data yields the distance traveled relative to a starting point. Thus, the motion and position of the wearer's head can be monitored by the sensors. In one embodiment the gyroscopes can be Murata part number ENC-05E gyroscopes giving an output in millivolts per degrees per seconds. Other gyroscopes can also be used.

Alternative embodiments may use a different sensor configuration. For example, a combination of gyroscopes and accelerometers may be used to enable monitoring the wearer's head position. Other position and motion sensors may be used.

User Interface

The head gear may enable the user to input information into the processor. Preferably, data entry can be accomplished through a user interface 20. One example of data input is whether the user wants the head gear activated. Preferably, a power on/off selector is provided in the user interface for this purpose. Another example of user data entry applies to embodiments adapted for sports training. The user may input the particular sport or application that the head gear is being used to monitor. For example, the user can input a "baseball" selection when the user desires to practice a baseball batting swing. After selecting the particular application, further information may be inputted into the head gear. For example, head gear adapted for use as a baseball batting trainer requires the user to input whether the user is left or right handed. This allows the processor to determine the preferred direction of head rotation. For example, rotations about the Z axis towards the catcher are "good" because, they indicate proper tracking of the motion of the ball towards the batter. Similarly, rotations about the Z axis away from the catcher are "bad". However, for a right-handed batter "good" rotations are clockwise, "bad" rotations are counter-clockwise. The situation is reversed for a left-handed batter. Thus, in this embodiment, the processor must know which situation exists in order to properly interpret the rotation data. In one embodiment the on/off switch is a dual function switch, controlling both the power and the right/left-handed selections. Other embodiments may have separate right/left and on/off switches.

Other user inputs to the head gear are possible. For example, the user could control such things as the volume level of an audible indicator, activating a save data setting or set up the head gear to judge head motion based on the skill level of the head gear user (e.g., novice or expert).

Indicator

Some embodiments comprise indicator 50 which provides both positive and negative feedback to the user of the head gear. The indicator 50 may provide, for example, audible signals to the wearer. In these embodiments the indicator 50 is, preferably, a piezo ceramic speaker. Drive to the speaker can be provided by one (or more) of the programmable I/O pins of the processor. The speaker is preferably driven by a square wave, the duration and frequency of which is controlled by the processor 30. Other drivers or signal indicators are possible. For example, synthesized or recorded speech may be incorporated into the indicator. Visible indicator signals, for example LED's or the like, are also possible.

The exact frequencies, duration, or the combinations of on and off times provided to the user are not important. The only requirement is that the user is able to readily differentiate between the various indications, in order to clearly discern the information being provided.

Some embodiments of the head gear employ several different audible indications. A "greeting" sequence may be sent when the head gear is turned on. If necessary, the user may make the various data inputs that may be desired (e.g., right/left-handed batter selection) during the greeting tone.

In some embodiments, an "armed" or "ready" indicator may be sent when the head gear has determined that the wearer is at rest and presumably has adopted the set or stance position in preparation to beginning the desired motion. The importance of establishing a wearer's starting position will be explained in the algorithm section below. The wearer waits for the "armed" indication before and between motions, to allow the head gear to properly monitor the motion.

In some embodiments, a "good" indicator, indicating proper head motion, can be sent during the monitored motion, and the actual indication being sent can be proportional to the degree of motion (e.g., as the degree of motion increases, the frequency of an audible tone increases or the frequency of a flashing LED increases). Alternative embodiments of the head gear may use a single fixed frequency audible indicator for "good" with the degree of "good" being indicated by a varying intensity sound instead of a varying frequency sound. The same may be applied to a visible indicator with an increase in visual signal intensity proportional to the degree of motion.

For some embodiments, a distinctive "bad" indicator may be sent when the head gear has determined that excessive "bad" or out of range motion has occurred. The "bad" indicator may interrupt any "good" indicator in progress, to indicate an improper head motion has occurred.

In some embodiments, silence, or no indicator, can be used to indicate either "good" or "bad" head motion depending upon the desires of the user.

Algorithm

For those embodiments sensing motion along two axes, preferably, the analysis of the head motion may be based upon the integration of the raw data collected from two sensors. These sensors are preferably two gyroscopes, one sensitive to motion about the X axis (i.e., head tilt) and one sensitive to motion about the Z axis (i.e., head rotation). As mentioned previously, the outputs of the gyroscopes may be proportional to angular speed of rotation so a single integration will yield distance traveled about an axis in degrees. For embodiments sensing motion along a different number of axes, the algorithm is similar, however, the number of sensors may vary.

An important point to consider is that, in some embodiments, this integration can be, preferably, deliberately imprecise. In these embodiments, the actual integrator is a "leaky" integrator. A small portion of the accumulated integration may be discarded after every update. This prevents small errors due to noise or a small error in the initial reference for the integration from being accumulated. The actual arithmetic is also not precise. A more exact numerical integration would require multiplication. A precise integration would require floating point rather than fixed point arithmetic. These both cost processor time. The analog to digital conversion is, preferably, limited to 8 bits of resolution. The actual sensor output can be subject to drift with temperature and time. All these factors can eventually result in a large error in the apparent position of the head, which can be further compounded over time. In these embodiments, the apparent position of the head will only be accurate for a short period of time, thus, the desire to "arm" the head gear before every practice motion. "Arming" the head gear means having the wearer assume a stance and remain still until that fact is recognized by the head gear. The armed indicator indicates to the wearer that the integrations have reset and restarted and the head gear has refreshed the position of the wearer's head and is ready for the start of the next practice motion.

Some embodiments of the head gear can be programmed to "remember" or store the sensor readings for a particular motion. Subsequent motions can be compared to the stored data. These embodiments may require additional processor memory capabilities as noted above. For example, in a baseball batting aid embodiment, the processor can store in memory the sensor data values that occur during a chosen swing. Subsequent swings can then be compared with the stored data as a training aid. The processor can automatically store a successful motion (e.g., by selecting an "auto-store" mode) or a successful motion can be selected, by the user, after the motion has been completed. For example, in the baseball training embodiment, a player might have completed a correct swing (e.g., satisfactory contact with the ball); the player can now select the "store" mode and the sensor data for the successful swing will be stored in the processor for comparison with subsequent swings. Alternatively, the user can select an "auto-store" mode where a correct swing is automatically stored in memory.

Figure 2:
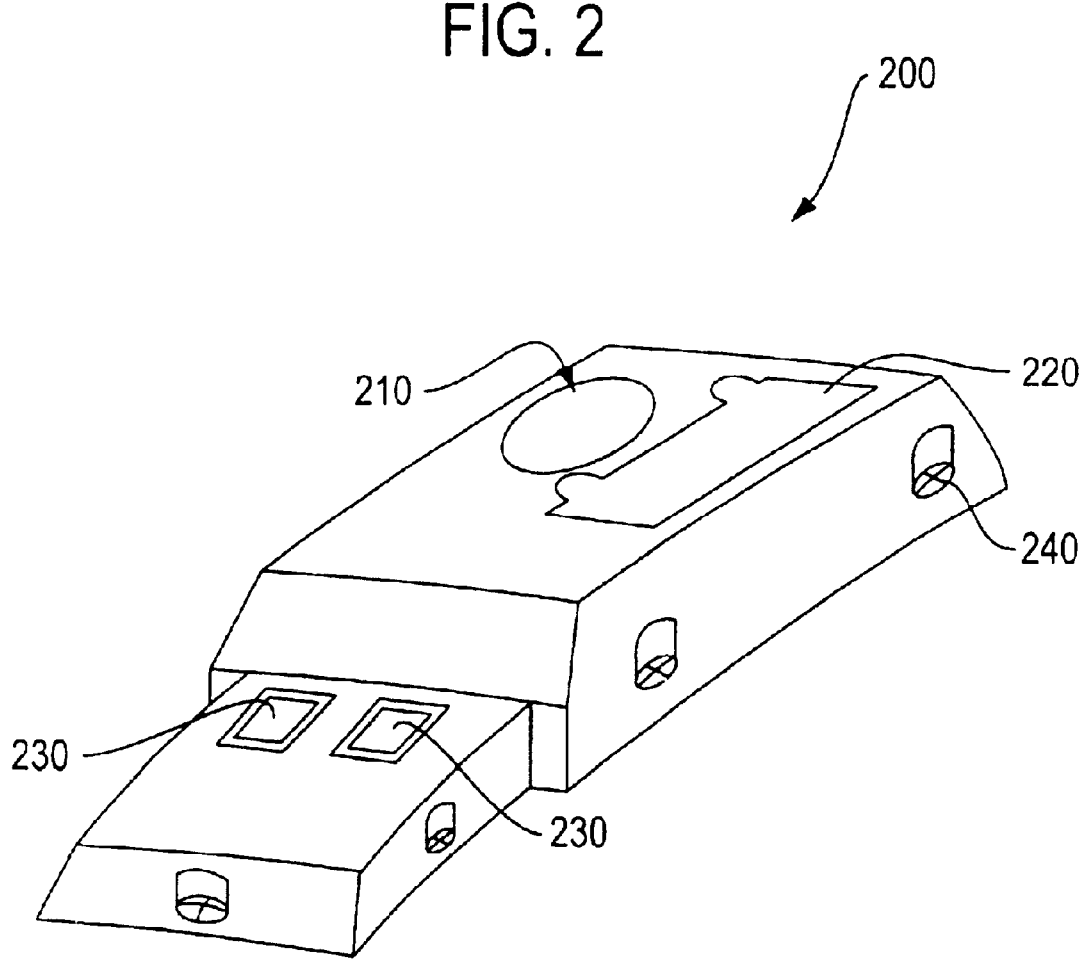
FIG. 2 is a schematic illustration of an attachable embodiment of the invention.

As shown in FIG. 2, the head gear may comprise a unitary construction. Contained within the head gear 200 are the components described above. The embodiment in FIG. 2, comprises an audible indicator, shown as a speaker element 210. A compartment 220 is provided to house a battery or similar power source. Switches 230 comprise the user interface portion. In the depicted embodiment two switches are shown, one for on/off and volume the other for left/right handed input. Other configurations of the user interface portion are possible. The head gear 200 may be attached to a suitable item of head wear prior to use. The attachment of head gear 200 may be carried out in any suitable fashion that does not significantly interfere with the wearer's performance. For example, fastening screws 240 are shown in FIG. 2 to enable attachment.

Figure 3:
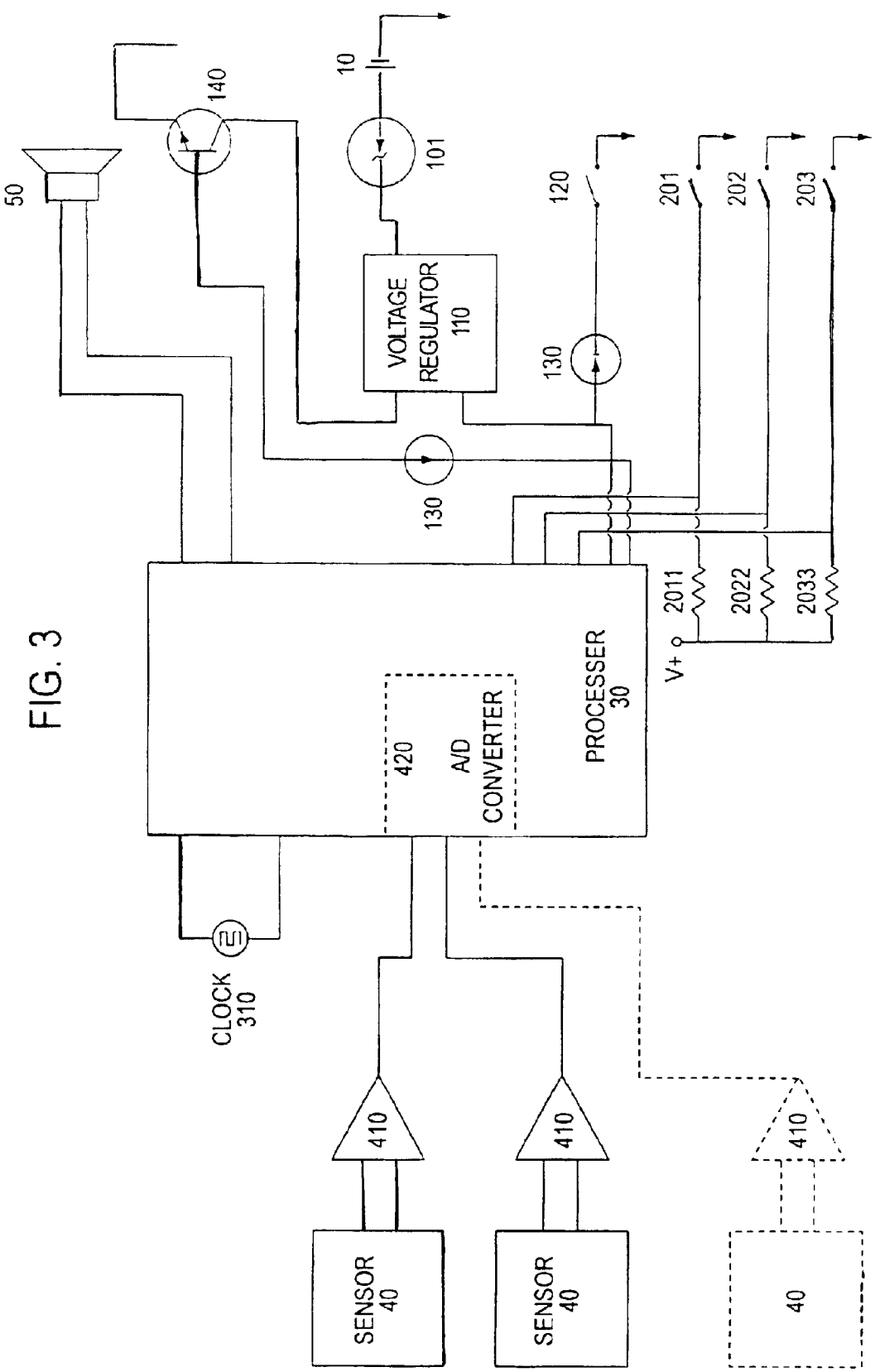
FIG. 3 is a schematic of the circuit for an embodiment of the invention.

A schematic diagram of one embodiment of the head gear is shown in FIG. 3. The number of sensors 40 used may vary according to head gear's intended application. The variability of the number of sensors is indicated in FIG. 3 by the sensor 40 shown in broken lines. The analog output of each sensor 40 may be amplified by an amplifier 410. The amplified sensor output may then serve as the input for an analog to digital (A/D) converter 420. For embodiments comprising a PIC type processor 30, the A/D converter 420 may be an integral portion of the processor chip. Clock 310 may also comprise an integral portion of the processor 30. Clock 310 provides a timer for the various time-out periods in the operation of the head gear. Indicator 50 is coupled to the output of processor 30. In FIG. 3, indicator 50 is represented schematically as an audible speaker. Other indicators, for example, a visible LED indicator, are also possible. Power for the head gear is supplied by power source 10, indicated as a battery in FIG. 3. Voltage from the power source 10 may be regulated by a voltage regulator 110. A protection device, for example, diode 101, may be used to protect the voltage regulator if power source 10 is inadvertently installed with the wrong polarity. Power on/off switch 120 may be provided to allow the user to turn the head gear on or off. Additional circuit devices, for example, diodes 130 and transistor 140, may be provided to enable a safe and effective supply of power to the head gear. In FIG. 3, the user interface is depicted as comprising switch elements 201, 202, 203. The switch elements 201, 202 and 203 are used for selecting a voltage level, determined by associated resistive elements 2011, 2022 and 2033. This voltage level may serve as input to the programmable I/O pins on the processor. In this manner, the processor can be programmed to enable the various functionalities described herein. The switch elements 201, 202 and 203 are represented as single position switches, but may comprise multiple position switches or other appropriate devices. The switches may be set to input certain values into processor 30. Other data input devices may be used, and the user interface may comprise more or less than three elements.

Sample Embodiments

The head gear described above can be adapted to perform as a head motion monitor for many applications. The following examples are included to illustrate some of the possible embodiments that the head gear can be programmed to monitor. Other embodiments will be apparent to those skilled in the art.

Baseball Training Aid

The head gear has application as a training aid in the sport of baseball. Preferably, this embodiment senses motion along the X and Z axes. The head gear can be programmed to monitor proper head motion as it pertains to the sport of baseball. For example, proper head motion is critical to good batting technique. The operation of the monitoring algorithm is, preferably, as follows. The arming algorithm looks for a small integration about both of the sensitive axes (e.g., X and Z). If the small integration persists for a programmed period of time, the batter is moving his or her head only very slightly. The head gear assumes that the batter has taken a stance and is ready for the next swing. The head gear is then "armed." While armed, the head gear constantly checks the value of the integrations about both of the sensitive axes (X and Z). Motion is deemed to have occurred if the value of the integration exceeds a programmed threshold about either axis. If a large "bad" rotation occurs before any downward tilt of the head occurs, the head gear concludes that the swing is incorrect and may send the "bad" indicator. If a downward tilt of the head occurs first, two things happen. The "good" indicator may be sent to the batter. The indication sent to the batter will be proportional to the degree of downward tilt and as the downward tilt increases the indication will change in either frequency or intensity to indicate to the player the degree of tilt. Recognition of the downward tilt may also start a timer. The period of the timer is programmable. The head gear looks for "bad" rotation during the time-out period. If "bad" rotation exceeds a programmable threshold before the timer expires, the "good" indication may be replaced by the "bad" indication. The head gear has determined that the batter's head has followed the front shoulder out, not allowing for the proper head/front shoulder separation during the swing. In particular, younger players have a tendency to look up too quickly to see where the ball has been hit. Looking up too quickly decreases the chances of achieving proper shoulder transfer during a swing. Some embodiments of the head gear may be programmed to include a long time-out period to help achieve proper shoulder transfer. When the timer expires, the head gear stops checking for rotation. This is to eliminate faulty bad indications from occurring due to motion of the head after the swing has been completed. Any rotation after this time is assumed to be after proper contact has been made with the ball, and the rotation is the result of the batter starting to track the hit ball (e.g., to determine where it lands). The sequence now restarts with the head gear once again looking to be armed.

The head gear can be adapted for use as a baseball fielding trainer. The proper technique for fielding a ground ball is for the player to keep his or her head down, watching the ball until it is secured in the player's mitt. Only after the ball is secured should the player look up to the place where the ball is to be thrown. Inexperienced players have a tendency to look up before the ball is secured. This often results in an "error" or missing the ball. The head gear can be programmed to signal the fielder to keep his or her head down until the ball is secured. The fielding embodiment may comprise a simplified design as head motion need only be detected along one axis (e.g., the X axis). Sensing along more then one axis may also be included in a fielding embodiment of the head gear. Similarly, the head gear can adapted for use as pitching trainer.

The head gear can also be adapted to train cricket batters to maintain proper head position. As the motion of batting a cricket ball is similar to batting a baseball, the program to monitor the head motion is also similar.

Figure 4:
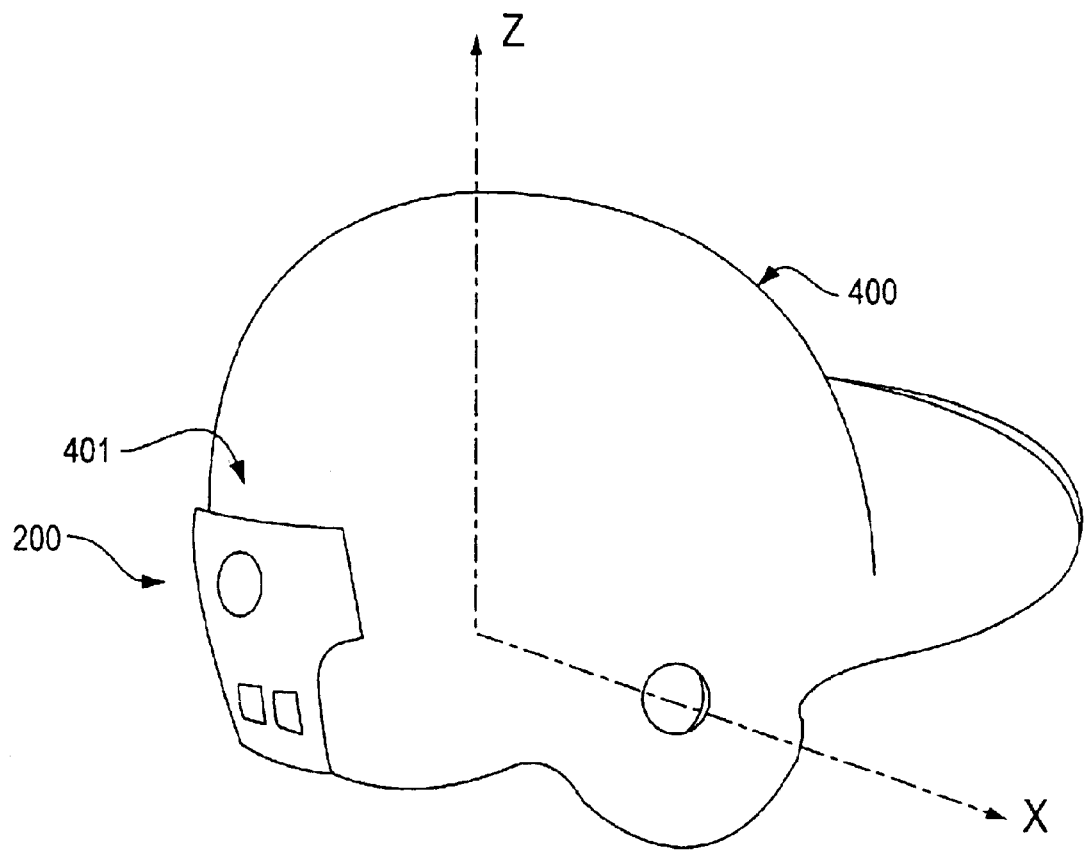
FIG. 4 depicts an embodiment of the invention as applied to the sport of baseball.

As shown in FIG. 4, the head gear 200 is attachable to an ordinary baseball batting helmet 400. The head gear may be mounted at the rear of the helmet 401 and interferes as little as possible with the normal use of the helmet. Alternatively, the head gear may be integrally formed into the batting helmet.

Hockey Training and Safety Aid

The head gear can also be adapted for use as a training aid for hockey players. Numerous actions occur in a hockey game that require the player to have proper head motion or position. Algorithms to monitor these heads motions can be programmed into the head gear, so that the motion can be practiced. For example, during a "face off" a player should keep his or her head down to watch the puck as it is dropped to the ice. If the player does not keep his or her head down, the head gear's indicators will alert the player that the head position is improper. In addition to practicing a face off, the head gear can be used to practice other activities that arise in the course of a hockey game. For example, a few situations that can be practiced using the head gear are: when tending goal a goalie's head should be down to watch the approaching puck, when a player is preparing to receive a pass the head should be down to watch the pass and control the puck with the stick (or skate), when shooting the puck a player should have the head down to watch the puck throughout the shot, when coming out of a quick turn while skating a player should have the head up, and when looking to pass the puck the head should be up. Some of these applications may be incorporated into an embodiment of the head gear that senses motion along one axis.

The head gear can be incorporated into a hockey player's safety equipment. As shown, generally in FIG. 5, the head gear 200 is adaptable to fit inside a normal hockey helmet 500 and, thus, offers the usual head protection of the normal hockey helmet. The head gear 200 may be fitted into the helmet 500 in between protective padding elements 510. Alternatively, the head gear 200 may be mounted on the outside of the hockey helmet in a fashion similar to the baseball embodiment as shown in FIG. 4. The head gear can be programmed to warn the player when his or her head is in a potentially dangerous position. In these embodiments more sensors may be included to detect motion along all three axes (e.g., X, Y and Z). For example, a player may risk neck and spine injuries by getting hit or "checked" with his or her head in the wrong position. The head gear will warn the player in advance that the head is in a potentially dangerous position and give the player a chance to correct the position.

The head gear can also be adapted to other sports similar to hockey. For example, the head gear can be programmed to provide training or safety information to participants of similar sports such as field hockey, lacrosse and soccer.

Tennis Trainer

The head gear can be adapted to provide training for certain movements in tennis. For example, the head gear can be programmed to help a player practice a tennis serve. When serving, initially the head should be up looking at the ball as it is tossed into the air. The head should remain up until the racket has contacted the ball and then the head should be looking down after contact with the ball. The head gear can also be programmed to practice the forehand and backhand strokes. During these motions the players head should be looking down at the ball and the point of contact with the racket. The head gear is programmed to give the player an indication of proper head position.

Figure 6:
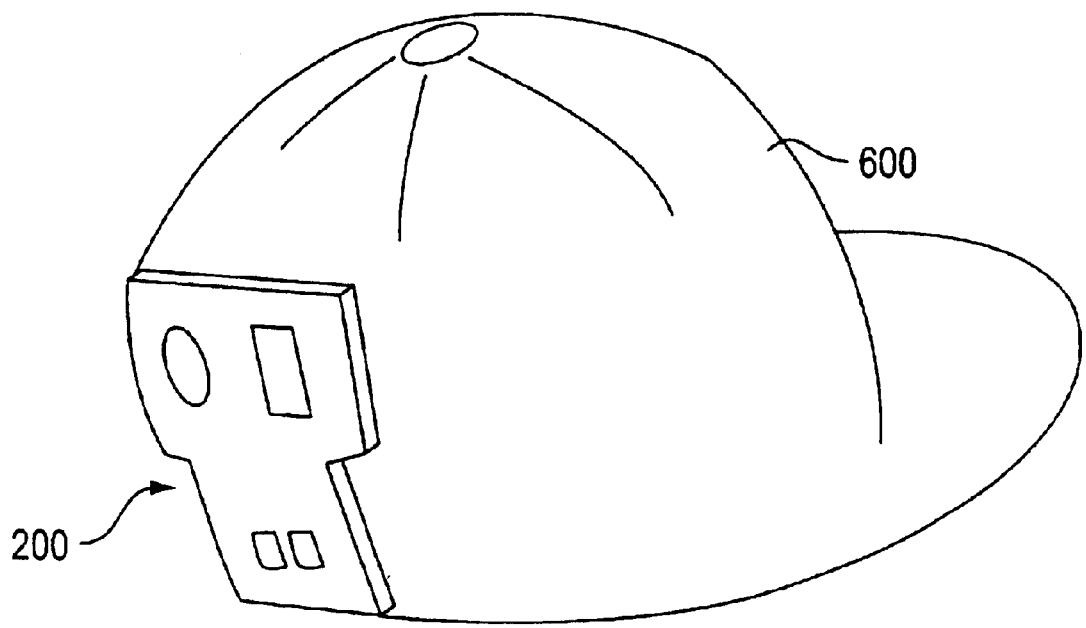
FIG. 6 depicts an embodiment of the invention attached to a cap or hat.

For this type of application, where a helmet is not normally worn, the head gear may be attached to a cap, hat, head band or other similar device to be worn while utilizing the head gear. Such a mounting is represented in FIG. 6. The head gear 200 may be attached to a cap or hat, for example, cap 600.

Football Training and Safety Aid

The head gear is adaptable to provide training for certain motions that occur in the sport of football. For example, punting and place kicking require that the player keep his or her eyes on the ball and head down during the kick. The head gear is programmed to indicate when this head position is or is not achieved.

The head gear can also be programmed to train proper blocking or tackling position. Proper form is with the player's head up and eyes open. For inexperienced players the tendency is to put the head down and close the eyes as a collision is approaching. At the least, this can cause a missed block or tackle; at worst, injuries can result. The head gear is programmed to give the player an indication of whether the head is up. When the head is properly up, the tendency is for the eyes to be open as well.

The head gear is incorporated into the same type of helmet as existing football helmets and offers the usual level of protection to the wearer. The head gear offers an additional level of protection to the wearer by alerting the wearer of improper head position. By notifying the wearer that his or her head is in a potentially dangerous position, the player can act to correct the situation and, thereby, avoid injury.

Figure 5:
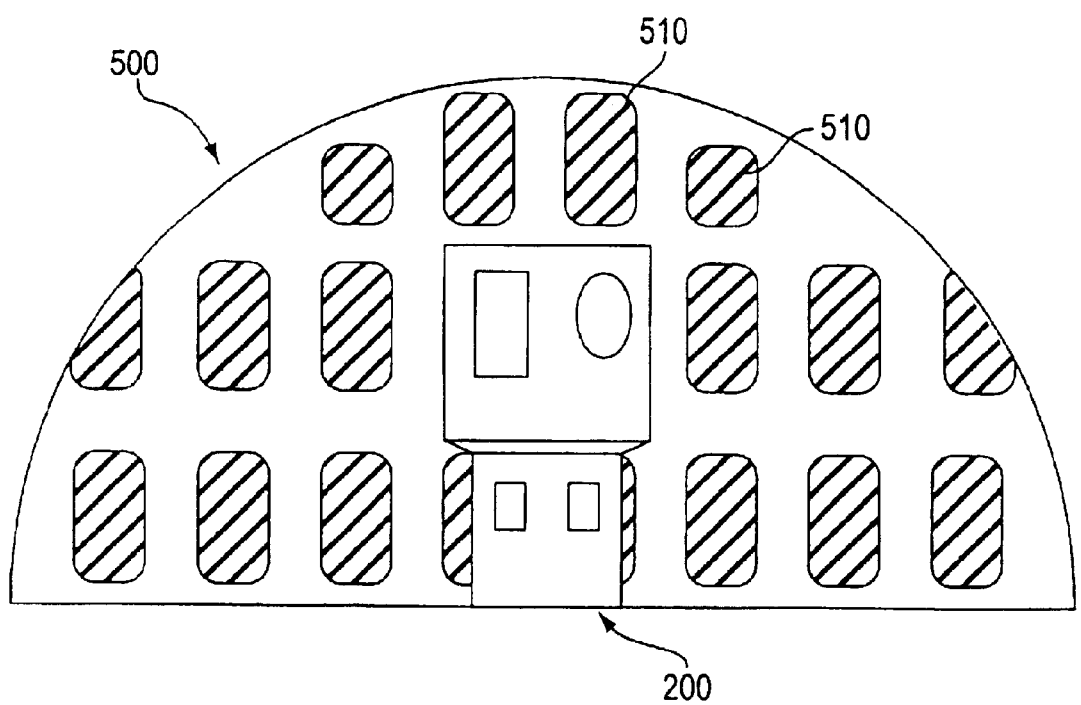
FIG. 5 depicts a partial cut-away view of an embodiment of the invention mounted within a protective helmet.

Mounting the head gear 200 inside an existing football helmet 500 is depicted schematically in FIG. 5. The head gear 200 may be mounted in between protective padding elements 510 inside the helmet so as to not interfere with the normal use of the helmet. Alternatively, the head gear may be mounted on the outside of the helmet in a manner similar to the baseball embodiment shown in FIG. 4.

Golf Swing Trainer

The head gear is adaptable to provide training for improving a golfer's swing. This may accomplished on multi-activity embodiments of the head gear by selecting, via user interface 20, a golf mode. Other embodiments may provide a dedicated golf only training device. In any case, the head gear is suitably equipped to provide an feedback to a wearer executing a golf club swing.

Contrary to popular belief, a golfer's head should not remain still during a proper golf swing. Golf experts such as Jimmy Ballard, in his book "How to Perfect Your Golf Swing," published by Golf Digest/Tennis, Inc., in 1981, and Jim McLean, in his book "The Eight Step Swing" published by Harper Perennial in 1994, emphasize that the golfer's head should not remain still during the swing. Proper head motion is for the head to execute its own miniature swing that follows the motion of the golfer' body. The head should move naturally with the spine during the swing. For example, prior to the beginning of the motion the golfer's head is preferably motionless and positioned to look at the point of contact with the ball so that the golfer may clearly see the ball and the point of future club impact. As the golfer begins the back swing part of the motion, the head will preferably follow the motion of the shoulders and spine and rotate approximately 20 to 25 degrees from its initial position. The head preferably will pause and remain in the approximately 20–25 degree position until the golfer reaches the apex of the back swing. Then, the head should follow the motion of the shoulders and spine into the forward motion of the swing until the initial position is reached. Preferably, the head motion should pause at the initial position while the ball is struck. After the pause at impact, the head may preferably rotate toward the target point to follow the path of the ball. During the entire motion the golfer's head is preferably inclined slightly downward or positioned to look at the point of club impact.

Some embodiments of the head gear may be programmed to monitor the above exemplary head motion. Preferably, the operation of the monitoring algorithm is as follows. The arming algorithm monitors for a small integration about the sensing axes. Any number of axes may be used to detect motion, however, the following description is of an embodiment for which motion is monitored about two axes (e.g., X and Z). Preferably, the golfer's head will be properly aligned prior to the swing when the golfer is in position and in a stance such that the golfer's body is erect and level through the hips, knees and shoulders. A small integration persisting for a pre-programmed period of time indicates that the golfer is moving his or her head only very slightly and is ready to begin the swing. When this condition occurs the head gear is armed. While armed the head gear constantly senses for motion about either of the sensing axes. Motion is deemed to have occurred if the integration value exceeds a pre-programmed threshold about a sensing axis.

For some embodiments, the head gear will monitor for backwards rotation of the head after the head gear is armed. As noted above, some embodiments of the head gear have a user selectable handedness switch (i.e., left handed or right handed) with which the golfer can indicate which direction will comprise a forward and which direction will comprise a backward rotation. Other embodiments may comprise pre-programmed handedness.

Some embodiments of the head gear may sense the backward head rotation to monitor that a pre-programmed limit is not exceeded within predetermined tolerances. Preferably, the pre-programmed backwards head rotation will have a limit set at approximately 20–25 degrees as measured from the rest (i.e., head looking at the ball) position. In some embodiments, this may be accomplished by setting a 22.5 degree limit with a tolerance of ±2.5 degrees. Other predetermined limit ranges and tolerances are possible. For example, some embodiments of the invention may include a user selectable limit value to allow each particular user to set a preferred limit value. Some embodiments may include a selectable skill level input switch that may, for example, decrease the tolerances for deviation with increasing skill level.

Preferably, the head gear will monitor for a pause in the backwards rotation. The pause should occur for a predetermined length of time before any forward rotation is sensed. As with the predetermined rotation limit, the predetermined pause time limit may be adjustable to accommodate user preferences and skill levels.

The head gear will sense the forward rotation of the golfer's head. Preferably, the forward rotation is monitored to ensure that the head returns to the initial position. At the point of club contact the golfer's head should remain relatively still throughout the period of club contact with the ball. Some embodiments of the head gear monitor to detect a pause during the motion while the club head strikes the ball. As with other aspects of the head gear, the forward rotation parameters and the pause period may be customized to accommodate user preferences.

Some embodiments of the head gear may continue to monitor the head motion to detect proper follow through motion of the golfer's head. For example, the head gear may monitor to detect a continued forward rotation as the golfer rotates his or her head to follow the motion of the ball towards the target.

Some embodiments of the head gear may monitor head position to ensure that an improper lifting or dropping of the head does not occur. For example, some embodiments of the head gear may monitor rotations about the X axis to detect whether the golfer has improperly lifted or dropped his or her head (i.e., rotated about the X axis) during the swing.

Throughout the motion, feedback may be presented to the golfer to indicate the degree of compliance of each swing with the pre-programmed parameters. As noted above, this feedback may comprise, audible, visual, verbal, or other indicators. Frequency, intensity, volume or other characteristics of the feedback may be varied to indicate, compliance, lack of compliance, degree of compliance and other aspects of the golfer's swing. Because motion of a golf swing is fairly rapid, distinguishable indicators may be used to indicate different conditions. For example, one alarm could indicate that the golfer over rotated during the back swing and another could indicate that the golfer did not pause during the period of contact with the ball. In this manner, the golfer may receive feedback information that indicates more precisely which elements of the swing were improper. Any combination of audible or visual or other alarms may be used to indicate the proper or improper motion of the various components of the head motion.

For this type of application, where a helmet is not normally worn, the head gear may be attached to a cap, hat, head band or other similar device to be worn while utilizing the head gear. Such a mounting is represented in FIG. 6. The head gear 200 may be attached to a cap or hat, for example, cap 600.

Skating Trainer and Safety Aid

The head gear is adaptable to provide training to improve skating ability. When learning to ice skate, roller skate or roller blade inexperienced skaters tend to put their heads down and look at their feet. This makes learning to skate harder because, it is difficult to maintain proper balance when looking at the feet. Keeping the head down also narrows the skater's field of vision. The narrow visual field adds to the danger of skating into an obstacle. The head gear is programmable to alert the skater to maintain upright head position. The head gear can be enclosed in a protective helmet (for example, as in FIG. 5) to offer the skater an additional level of protection.

Boxing Training Aid

The head gear is adaptable to train a boxer to keep the proper head position. Boxers should keep their heads and chins tucked down when fighting. Doing so minimizes the impact of punches landing on the boxer's face, a desirable result. The head gear can be incorporated into the normal boxing head gear and programmed to alert the boxer when his or her head comes out of the proper position. For example, if the head tilts too far up (e.g., along the X axis) an indication may be given to the fighter.

Bowling Trainer

The head gear is adaptable to indicate proper head position to a bowler. A bowler's head must be still and slightly tilted downward through the approach to the starting (foul) line, through the delivery of the ball and through the follow through motion. The head gear is programmed to indicate whether a bowler has performed the correct head motion.

For this type of application, where a helmet is not normally worn, the head gear may be attached to a cap, hat, head band or other similar device to be worn while utilizing the head gear. Such a mounting is represented in FIG. 6. The head gear 200 may be attached to a cap or hat, for example, cap 600.

Billiards or Pool Training Aid

The head gear is adaptable to aid a billiards or pool player in maintaining proper head position. When executing a proper pool shot the player's head should point slightly down and remain relatively still. The head gear is programmed to indicate when this proper position is maintained.

For this type of application, where a helmet is not normally worn, the head gear may be attached to a cap, hat, head band or other similar device to be worn while utilizing the head gear. Such a mounting is represented in FIG. 6. The head gear 200 may be attached to a cap or hat, for example, cap 600.

Archery or Shooting Aid

The head gear is adaptable to be used as a training aid for archery and shooting sports. The head gear can be programmed to monitor the proper head positioning to enable successful completion of archery or shooting motions.

For this type of application, where a helmet is not normally worn, the head gear may be attached to a cap, hat, head band or other similar device to be worn while utilizing the head gear. Such a mounting is represented in FIG. 6. The head gear 200 may be attached to a cap or hat, for example, cap 600.

Driver Alertness Aid

Many automobile accidents are caused when the driver falls asleep at the wheel or when the driver is distracted and looks away from the road for too long. Another embodiment of the head gear can be programmed to alert the driver of this dangerous condition. The optimal position for an alert driver's head is upright and facing forward. Some short term "head checking" motion where the driver looks to the side, for example, to see if neighboring lanes are clear is also permissible. When a driver falls asleep, or becomes distracted, his or her head will deviate from the optimal position. Multiple sensors may be provided to detect head motion in any direction. If the sensors determine that the head has been in a non-optimal position for too long, the program will activate the indicator to alert the driver to revert to the correct position.

For this type of application, where a helmet is not normally worn, the head gear may be attached to a cap, hat, head band or other similar device to be worn while utilizing the head gear. Such a mounting is represented in FIG. 6. The head gear 200 may be attached to a cap or hat, for example, cap 600. Alternatively, the head gear may be incorporated into a protective helmet (for example, as in FIG. 5) and may offer an additional level of safety to the driver.

Pilot Alertness Aid

When an aircraft is in a turn and a pilot's head is positioned at an angle with respect to the vertical of the centerline of the aircraft, disorientation can occur. The head gear can be incorporated into a pilot's head gear to provide an alarm as to improper head position. The head gear may be programmed to act as a warning device. The pilot may be provided with a head position information only if there is prolonged consistent angle of bank turning so that the pilot is aware that although his or her sense of balance may suggest straight and level flight, the aircraft is actually still turning and descending.

Multi-Piece Head Motion Sensing Embodiment

Figure 16:
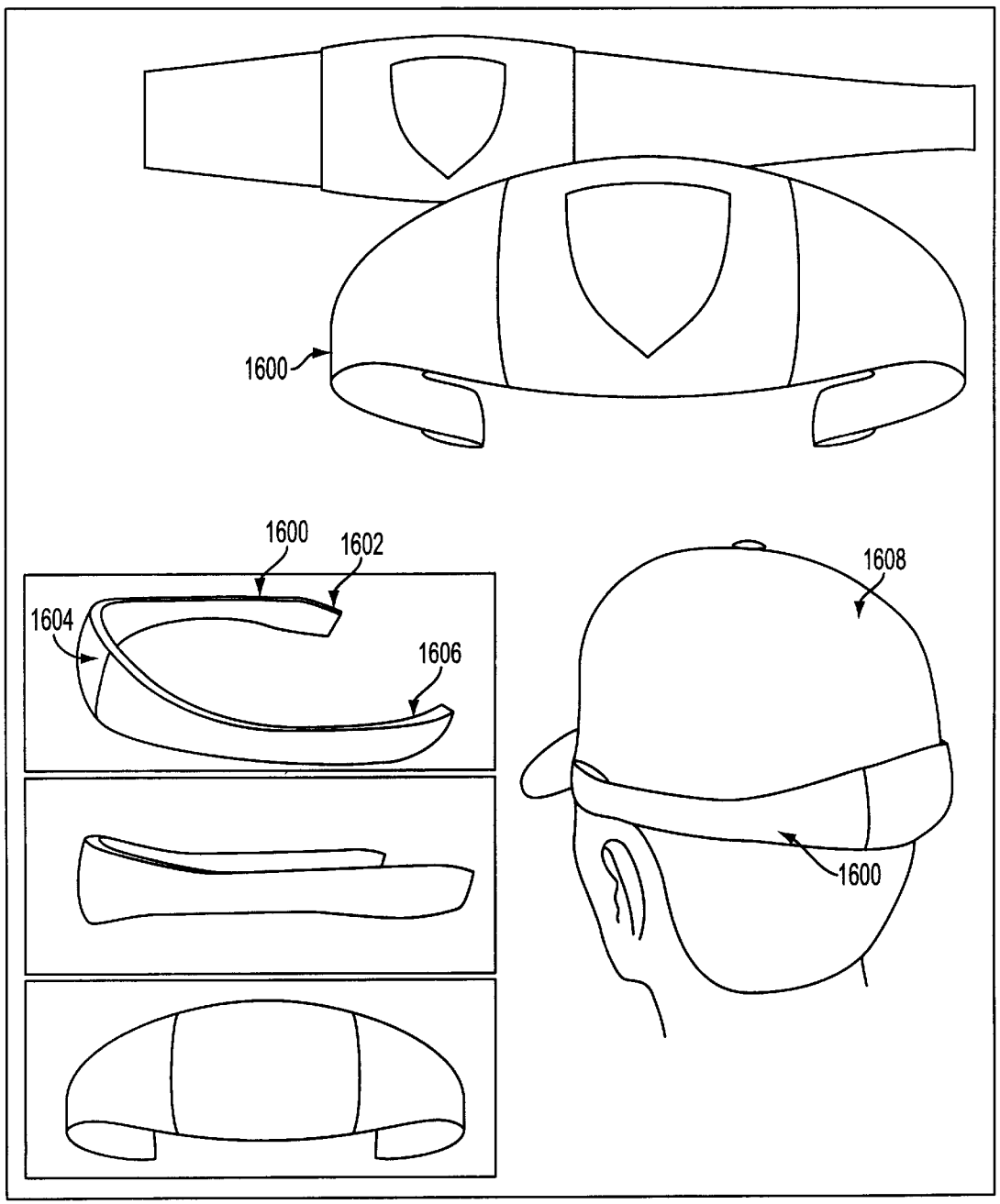
FIG. 16 is a representation of a head band apparatus according to another embodiment of the invention.

FIG. 16 shows a head motion sensor headband according to one embodiment of the invention. As shown, the head band 1600 may comprise a partial-ring like structure that may be worn on the head. The head band 1600 may comprise any suitable material that enables a comfortable fit and provides sufficient protection for the components within. For example, head band 1600 may comprise plastic, leather, metal, fiber, or other suitable material. Head band 1600 may be manufactured in an number of sizes to fit a wide variation of head sizes and shapes (e.g., adults, children, teenagers, men, women, etc.).

In some embodiments, head band 1600 may house sensor nodes or modules that contain head motion sensors. The head band 1600 may comprise any suitable number of sensor nodes to detect the motion of the wearer's head. For example, one embodiment of the head band 1600 includes three sensor nodes, which are indicated at 1602, 1604 and 1606. The three nodes may be located at roughly the back and two sides of the head band 1600 (i.e, at 90°, 180°, and 270° around the ring). Such a configuration positions the nodes on the wearer's head at substantially the the back of the head, and over each ear at the sides of the head. Other locations for the sensor nodes are possible.

Figure 10:
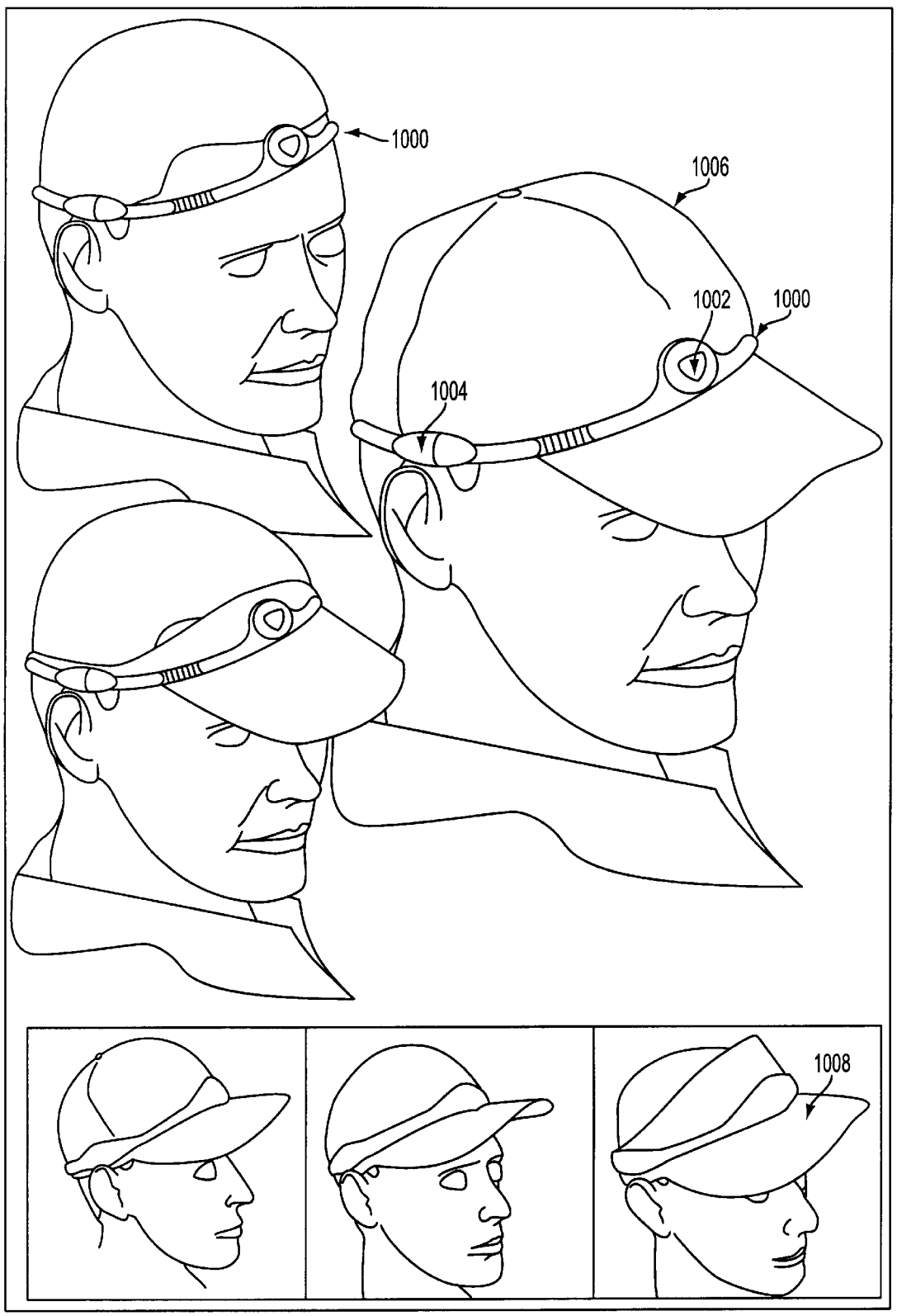
FIG. 10 is a representation of a head band apparatus according to one embodiment of a multi-piece head motion sensing system.

FIG. 10 shows a head motion sensor headband according to one embodiment of the invention. As shown, the head band 1000 may comprise a full-ring like structure that may be worn on the head. The head band 1000 may comprise any suitable material that enables a comfortable fit and provides sufficient protection for the components within. For example, head band 1000 may comprise plastic, leather, metal, fiber, or other suitable material. Head band 1000 may comprise an adjustable sizing mechanism, for example, a strap, or elastic band, or may be sized to fit standard hat sizes.

In some embodiments, head band 1000 may house sensor nodes or modules that contain head motion sensors. The head band 1000 may comprise any suitable number of sensor nodes to detect the motion of the wearer's head. For example, one embodiment of the head band 1000 includes four sensor nodes, two of which are indicated at 1002 and 1004. The four nodes may be located at roughly the front, back and two sides of the head band 1000 (i.e, at 0°, 90°, 180°, and 270° around the ring). Such a configuration positions the nodes on the wearer's head at substantially the front of the forehead, the back of the head, and over each ear at the sides of the head. Other locations for the sensor nodes are possible.

In some embodiments, each node (e.g., 1002, 1004, 1602, 1604, 1606) may house appropriate sensors. The sensors may comprise gyroscopic sensors, accelerometer sensors, or a combination of the two. Other sensors are possible provided they detect rotational or translational motion of the head. Some embodiments of the head band 1000, 1600 include an accelerometer and a gyroscope sensor in each node (e.g., 1002, 1004, 1602, 1604, 1606).

As shown in FIGS. 10 and 16, the head band 1000, 1600 may be worn over existing head ware such as cap 1006, 1608 and visor 1008. Other embodiments of the head gear may comprise a head band 1000, 1600 integral with a cap or other head wear. Of course, head band 1000, 1600 may be worn without any accompanying head gear at the wearer's discretion.

Figure 11:
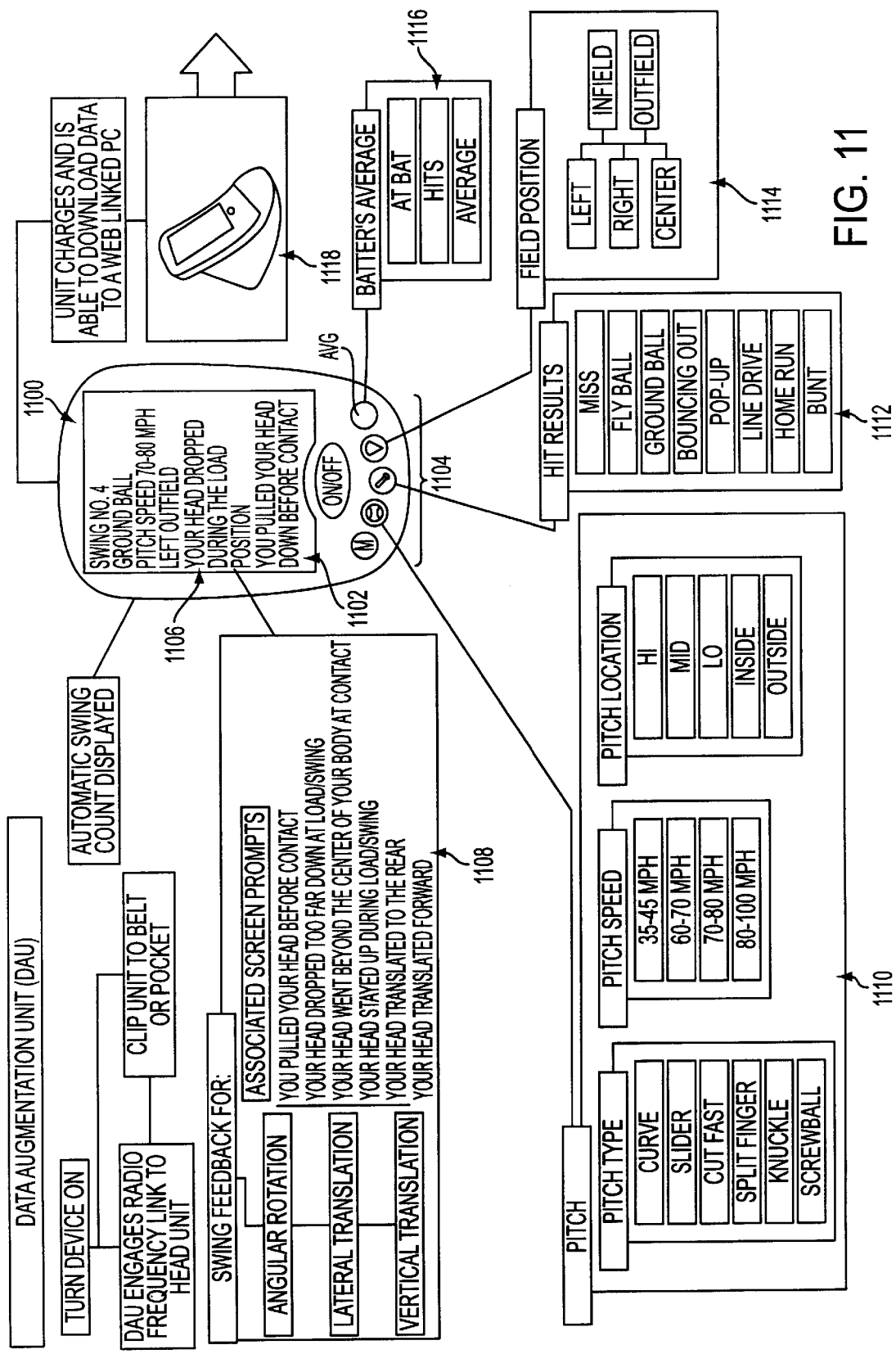
FIG. 11 is a representation of a data augmentation unit (DAU) according to one embodiment of the invention.

FIG. 11 shows a DAU 1100 according to an embodiment of the invention directed to baseball. As shown, DAU 1100 may comprise a portable processor based device with a display 1102 and a user interface 1104. Some embodiments of DAU 1100 may comprise a transmitter/receiver for communicating with the head gear sensors (e.g., 1002, 1004). For example, some embodiments may comprise a radio frequency (RF) link between DAU 1100 and head band 1000, 1600. Some embodiments of DAU 1100 may include ports or connectors to enable uploading of data, power source charging, communication with head gear 1000, 1600, or the like.

In some embodiments, processing functions may be enabled in the DAU using a suitable microprocessor. For example, an ADuC812 microcontroller (e.g., a PIC), manufactured by Analog Devices™ Corporation may be used for processing. Other microprocessors are possible. DAU 1100 may comprise other processor related features such as random access memory (RAM) and other onboard memory.

As noted above, some embodiments of DAU 1100 may include a display 1102. Display 1102 may comprise any suitable device for displaying visual information to a user. For example, display 1102 may comprise a liquid crystal display (LCD) screen, active or passive matrix displays, light emitting diode (LED) displays, mini cathode ray tubes (CRTs), or other suitable display device.

In some embodiments, display 1102 may provide text feedback messages as indicated at 1106. For the baseball DAU embodiment shown in FIG. 11, the feedback messages may comprise any of the messages indicated at 1108. Of course, other feedback messages may be used. In addition, the feedback messages may be displayed in languages other than English, by representative images, or other appropriate technique that relays the head motion feedback to the wearer.

In addition to display 1102, some embodiments of DAU 1100 may include a speaker, buzzer, bell, beeper, or other mechanism for transmitting audible feedback to the wearer. Some embodiments of the DAU 1100 may include a vibrator or other touch perceptible feedback indicator.

As noted above, some embodiments of DAU 1100 may include a user interface 1104. User interface 1104 enables a user to input information into DAU 1100. For example, DAU 1100 may comprise a number of buttons that provide access to menus or other lists of possible data input. Some embodiments of DAU 1100 may enable user input via display 1102 and a touch screen or stylus with which information can be written on display 1102 and recognized by suitable software.

In some embodiments, user interface 1104 enables the entry of data related to the physical activity being performed. For example, in an embodiment of DAU 1100 directed to baseball, user interface 1104 may enable the user to enter data related to the physical activity of batting a pitched ball. For example, user interface 1104 may provide a button or other selection device that is linked to a menu 1110 related to the type of pitch thrown at the batter (e.g., pitch type, pitch speed, pitch location, etc.). In addition, user interface 1104 may provide a button or other selection device that is linked to a menu 1112 related to the result of the batter's swing. Similarly, a button or other selection device may be linked to a menu 1114 related to the trajectory of any batted balls. Other inputs, such as batter's batting handedness, batter's skill level, date of batting session, type of feedback (e.g., audible, silent, visible, during activity, after activity, etc.), etc., are also possible.

User interface 1104 may also comprise buttons or other selection devices that enable the batter to extract data from DAU 1100. For example, user interface 1104 may provide a button or other selection device that is linked to a menu related to batting average. In some embodiments, user interface 1104 may also be used to display a calculation of the batter's current batting average, number of fly balls hit, number of hits to a particular spot (e.g., left field), or other data stored or processed by DAU 1100.

Some embodiments of DAU 1100 may comprise a mechanism to enable DAU 1100 to interface with other processor devices (e.g., a PC). For example, some embodiments may include a cradle 1118 comprising a socket or other connector that DAU 1100 connects with to allow communication with other processor devices. Communication between devices may be accomplished in any suitable manner. For example, communication may be via physical cable or wire connection, wireless connection, infrared connection, or other suitable communication technique. In addition, cradle 1118 may enable recharging of DAU 1100 power supply as is known in the art.

Figure 12:
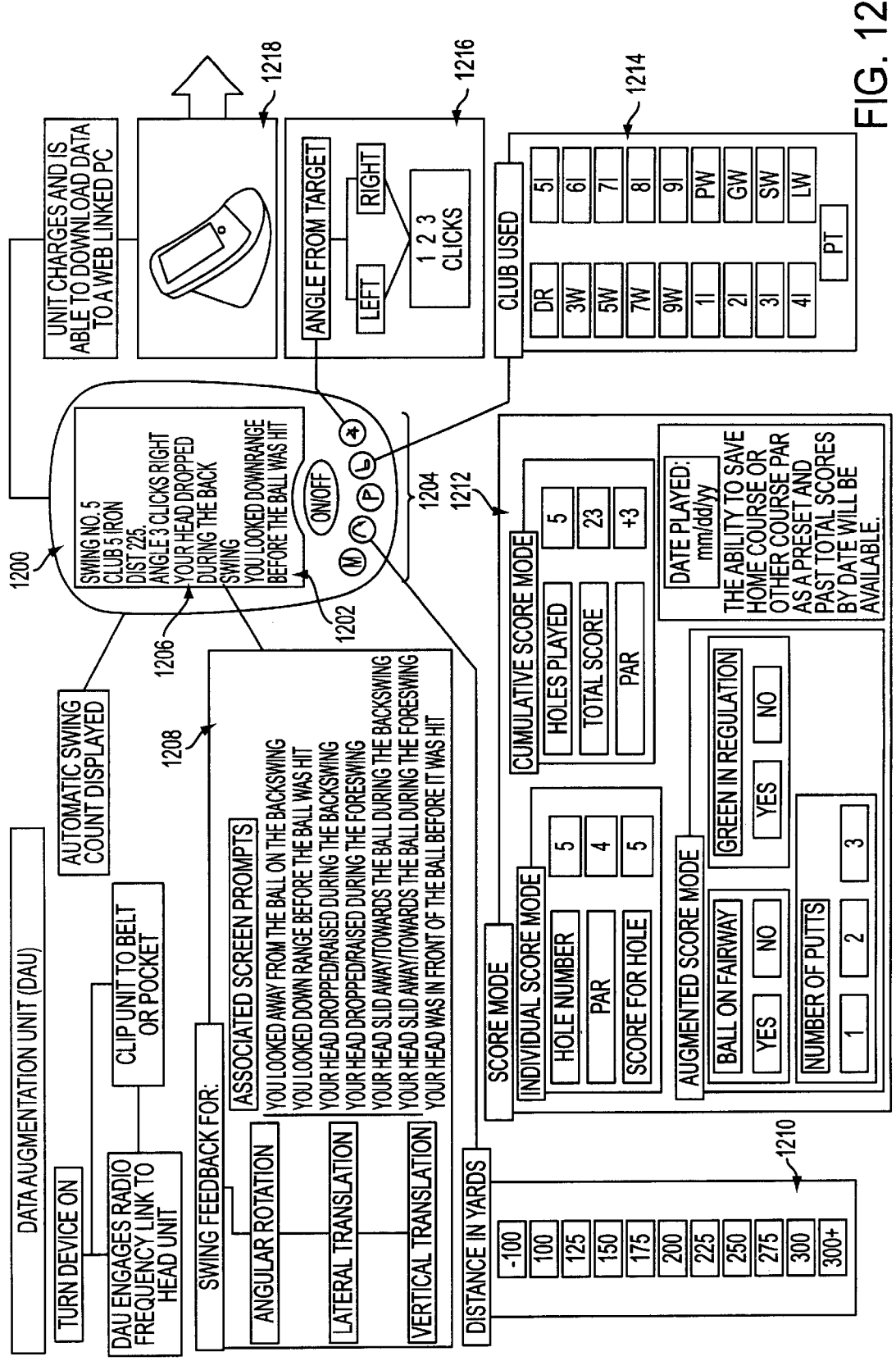
FIG. 12 is a representation of a DAU according to another embodiment of the invention.

FIG. 12 shows a DAU 1200 directed to a golf embodiment of the present invention. In some embodiments of the invention, DAU 1100 and DAU 1200 may comprise devices dedicated to the monitoring of the particular physical activity (e.g., baseball or golf). As discussed herein, other embodiments of the invention may comprise a "universal" DAU that is programmable to monitor any number of physical activities. In addition, some embodiments of the invention comprise a DAU that is a separate stand alone palm sized computer or other processor device for which software, head gear (e.g., head band 1000, 1600) and other accessories as necessary for each physical activity may be acquired separately.

As shown in FIG. 12, DAU 1200 may comprise a display 1202 and a user interface 1204 similar to the display 1102 and user interface 1104. Similarly, DAU 1200 may display text feedback messages 1206 related to the golfer's head movement. Of course, other suitable messages, for example, those listed on menu 1208, may be displayed as appropriate.

Some embodiments of DAU 1200 may comprise a user interface that enables the entry and retrieval of golf related information. For example, some embodiments of user interface 1204 may provide buttons or selection devices to access a menu 1210 related to the distance of the golf shot, a menu 1212 relating to the golf score, a menu 1214 related to the golf club used to make the shot, a menu 1216 related to the angle from the target, and other information related to golfing.

As noted above, user interface 1204 may also comprise buttons or other selection devices to enable a user to select other activity related features. For example, in a golf embodiment, user interface 1204 may enable a user to select the type of shot (e.g., drive, putt, chip, etc.), the user skill level (e.g., beginner, intermediate, amateur, pro, etc.), the player's handedness, the type of feedback (e.g., silent, audible, instantaneous, delayed, etc.), and other features.

Some embodiments of the invention may include a cradle 1218 or other mechanism to facilitate transfer of data and files to another device. As described above, cradle 1218 may also enable power source recharging.

Figure 7:
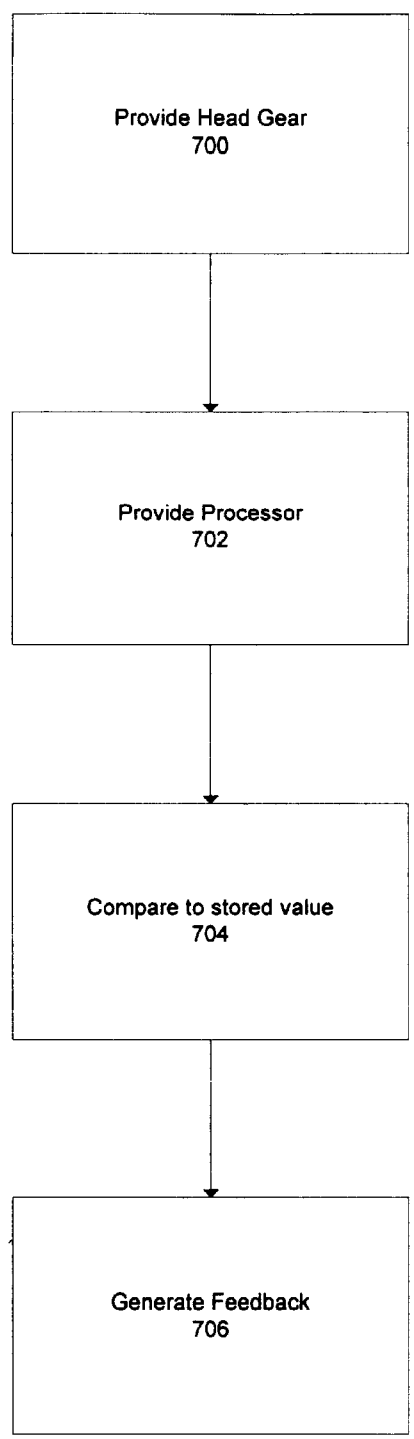
FIG. 7 is a flow chart of an overall method according to one embodiment of the invention.

FIG. 7 is a schematic representation of the overall method for providing head motion feedback to a user engaged in a physical activity according to one embodiment of the invention. As shown in FIG. 7, the head motion sensing process may initiate, as indicated at step 700, with the user donning the head motion sensing head gear (e.g., head band 1000, 1600). At step 702 the user may activate the processor portion of the head motion sensing apparatus (e.g., DAU 1100 or 1200). Of course, the relative timing of steps 700 and 702 may be different. For example, the user may activate the processor portion first (e.g., 702) and then don the head gear (e.g., 700). Other orderings for these steps are possible.

Upon initiation of a physical activity, the head gear and processor communicate to monitor the user's head motion during the performance of the activity. The head gear and processor cooperate, as described herein, to collect data corresponding to the path of the user's head motion. At step 704, the collected head motion data may be compared to a predetermined head motion. In some embodiments, the predetermined head values may be stored in the memory and are representative of desirable head motion paths.

At step 706, the result of the comparison is used to determine the type of feedback generated, for example, at step 706. As discussed above, different deviations (e.g., over rotation, under translation, too much elevation, etc.) of the head motion may cause different feedback signals.

Figure 8:
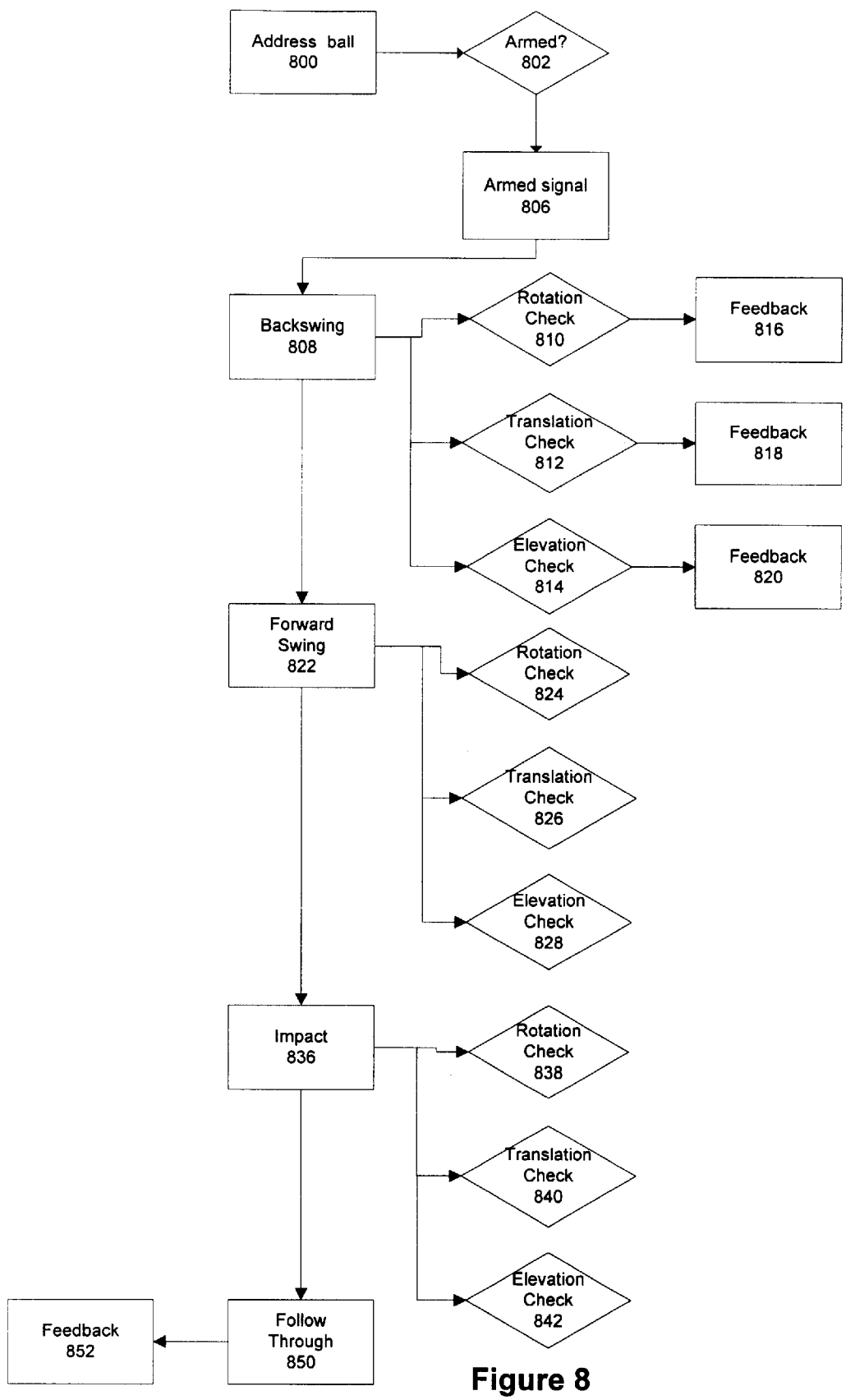
FIG. 8 is a flow chart of one embodiment of the invention related to head motion sensing during the physical activity of golf.

FIG. 8 shows a more detailed flow chart representing generation of feedback for an embodiment of the invention directed to monitoring head motion during the physical activity of hitting a golf ball. As shown in FIG. 8, the physical activity of hitting a golf ball typically initiates, as indicated at step 800, when the player addresses, or stands facing the ball. Some embodiments of the head gear perform a check at step 802 to determine if the head gear is armed and ready to take data. Arming the head gear may comprise the user holding his or her head, and thus, the head gear substantially stationary for a predetermined period of time (e.g., two seconds). Other methods of arming, for example, a switch or reset button, are also possible.

In some embodiments, if the head gear successfully arms, an armed signal may be generated as indicated at 806. Conversely, if the head gear fails to arm, the wearer will be alerted to that condition by the lack of an armed signal. Armed signal 806 may comprise any suitable signal (e.g., audible tone, visible display, or vibration) that indicates to the wearer that the unit is ready to take data.

Optionally, if the head gear fails to arm a feedback signal may be generated as indicated in phantom at 804. As noted above, the feedback signal 804 may comprise a variety of signals such as audible noise, visible displays, vibration, or other suitable signal.

Once the head gear is armed, the user may proceed to perform the physical activity. In an embodiment directed to a head motion monitor for golf, the user may proceed with a backswing portion of the motion as indicated at 808. As noted above, certain head positions and movements are known to be conducive to a successful golf swing. The path of motion that corresponds to this predetermined path may be stored in the processor (e.g., DAU 1200). The head motion sensors (e.g., 1002, 1004, 1602, 1604, etc., mounted in headband 1000, 1600) collect data pertaining to the golfer's head motion during the swing. The collected data is compared to the predetermined path. For example, a rotation check may be performed as indicated at 810 to determine the degree of compliance between the detected head rotation and the stored predetermined path rotation. Similarly a translation (e.g., linear movement of the head) check may be performed as indicated at 812 and an elevation check (e.g., lifting or lowering the head) may be performed as indicated at 814.

In some embodiments, comparisons 810, 812, and 814 may be followed by an immediate and appropriate feedback (e.g., 816, 818, and 820, respectively). As noted above, feedback may comprise an audible, visual, or other sensory signal that indicates to the user the results of the comparison. Feedback may be positive (e.g., the sensed head motion matched the predetermined path) or negative (e.g., the sensed head motion deviated from the predetermined path). In addition, feedback may be varied according to the degree of compliance (or non-compliance) with the predetermined path (e.g., louder feedback for grossly deviant head motion, softer feedback for almost conforming head motion). In some embodiments, feedback may be rendered substantially simultaneous with the actual physical motion (e.g., while the golfer is swinging) or at a later time (e.g., after the swing is completed). Other variations for the delivery of feedback will be apparent to those of skill in the art.

Continuing with the golf example embodiment shown in FIG. 8, after the backswing the golfer's motion should proceed to a forward swing motion as indicated at 822. Again, sensors collect data regarding the golfer's head motion and compare that sensed motion to a predetermined stored path (e.g., rotation check 824, translation check 826, and elevation check 828).

In some embodiments, the monitored physical motion occurs in such a brief time period (e.g., fractional seconds) that it is preferable to defer the issuance of feedback to some determinable point in time after the motion had completed (e.g., 2 second after completion of the motion) as indicated at feedback 852. In other embodiments, appropriate feedback may be generated contemporaneously with the result of the comparisons.

For some physical activities, certain points in the activity are useful reference points at which to measure head motion or position. For example, during the act of hitting a golf ball, one useful monitoring point may occur at the point of impact with the ball. When evaluating a golfer's swing, it is often useful to know the position of the golfer's head at the point of impact. In some embodiments, the head gear (e.g., headband 1000, 1600) or the processor (e.g., DAU 1200) may comprise a sensor to detect a set point in the motion that indicates the head position at a specified point in the motion. For example, in the golf embodiment shown in FIG. 8, the head monitoring system may comprise a sensor to detect the point of contact with the ball. The point of contact sensor may comprise any suitable sensor that detects that the ball has been hit. For example, a microphone may be incorporated into head band 1000, 1600 or DAU 1200 to detect the sound of the ball being struck, a transducer may be included in the system to detect the impact of the club with the ball, an optical beam (e.g., motion sensor) may be used to detect the movement of the ball, or other suitable point of contact sensor may be used.

In some embodiments, the point of contact sensor is used to flag, or otherwise mark, simultaneously collected head motion data points, so that an evaluation of the head motion at impact may be carried out as indicated at 836. At step 836 the head gear may perform a comparison of the sensed head motion with the stored predetermined path as indicated at rotation check 836, translation check 840, and elevation check 842. As above, associated feedback signals may be generated as a result of the comparisons as indicated at feedback 852 or generated contemporaneously with the result of the comparison.

For some physical activities (e.g., golf) the motion continues past the point of impact to a follow through motion as indicated at 850. For some embodiments, monitoring of head motion continues throughout the follow through 850 and may perform the rotation, translation and elevation checks as discussed above. Similarly, feedback signals may be generated for the follow through portion of the motion and generated as indicated at 852.

Figure 9:
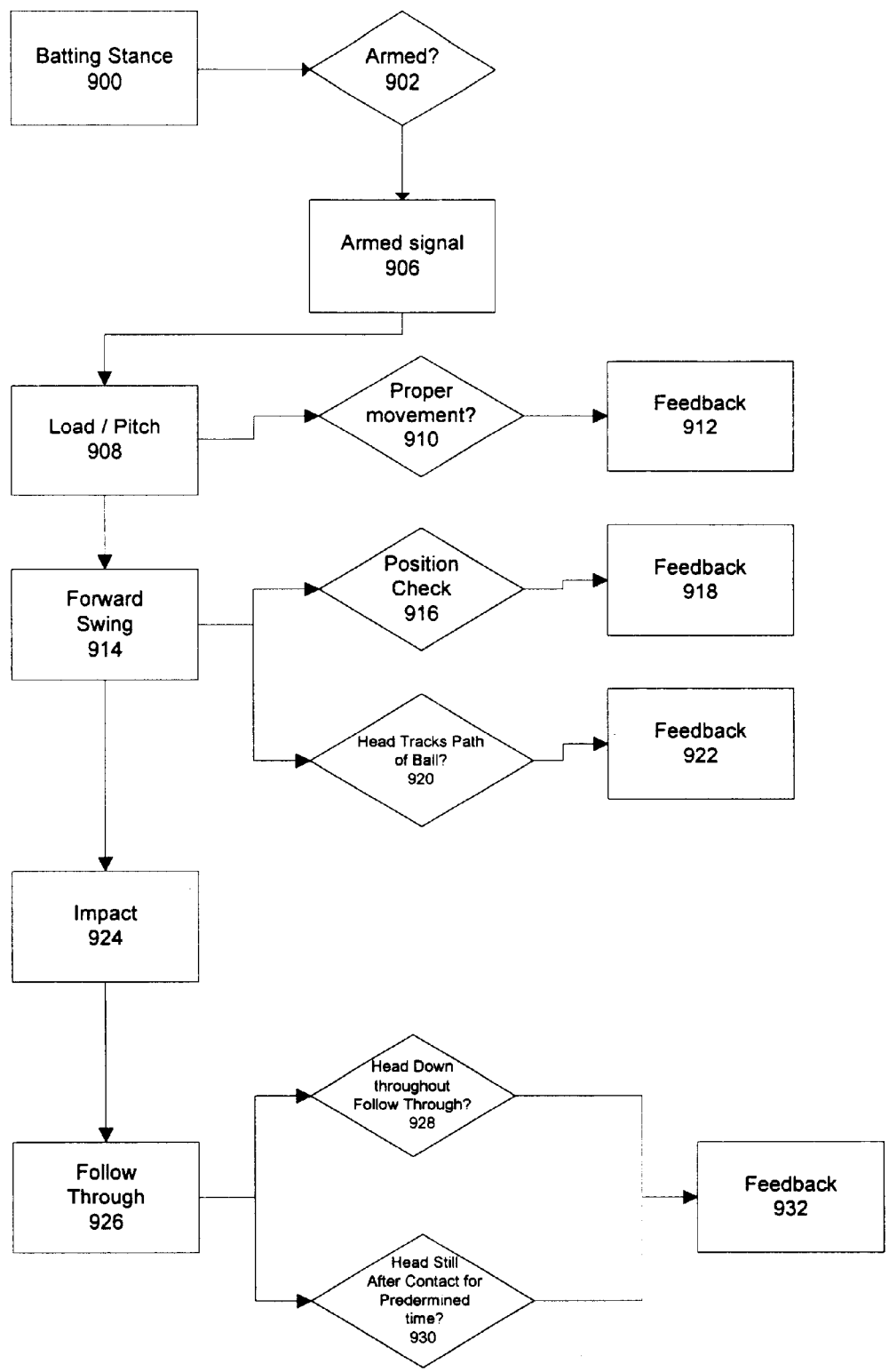
FIG. 9 is a flow chart of one embodiment of the invention related to head motion sensing during the physical activity of batting a ball.

FIG. 9 shows a more detailed flow chart representing generation of feedback for an embodiment of the invention directed to monitoring head motion during the physical activity of hitting a pitched ball. For this embodiment, the process may initiate when the batter assumes a batting stance as indicated at step 900. In some embodiments, the next step is for the head gear to be armed (e.g., by holding still, pressing a reset, flipping a switch, etc.) as indicated at step 902. In some embodiments, if the head gear successfully arms, an armed signal may be generated as indicated at 906. Conversely, if the head gear fails to arm, the wearer will be alerted to that condition by the lack of an armed signal. Armed signal 906 may comprise any suitable signal (e.g., audible tone, visible display, or vibration) that indicates to the wearer that the unit is ready to take data.

Optionally, if the head gear fails to arm, or if the head gear fails to arm before a predetermined event (e.g., detection of head movement before armed, passage of time, etc.), a feedback signal may be generated as indicated in phantom at 904. As noted above, the feedback signal 904 may comprise a variety of signals such as audible noise, visible displays, vibration, or other suitable signal.

Once the head gear is armed, a batter may enter the load at pitch phase of the swing as indicated at 908. As used herein, the load at pitch phase refers to the motion of the batter in anticipation of the pitch being delivered. Typically, load at pitch motion may be different for different batting styles and may involve a the batter shifting body weight over a back foot (with the front foot being the foot facing the pitcher), standing with balanced weight over both feet and slightly turning the front knee and foot, standing with some weight over a back foot, or a combination of the above. In addition, load at pitch motion may include a slight raising of the hands or other arm motion in preparation to swinging the bat. For example, a baseball batter's head turns (or moves) forward (accelerates) and down on the swing. Preferably, the head does not move past a midpoint of the body (e.g., a line from the middle of the head to the navel) or the middle of the chest. The other half of the body rotates up to and about the established head axis on the swing. Preferably, the batter's head may pass the midpoint of the body only when a full swing is not executed and the head follows the ball into the catcher's glove. As discussed above, a comparison may be made at step 910 between the batter's sensed head motion and a predetermined path for desirable head motion. Feedback 912 may be generated as a result of the comparison. Feedback 912 may be generated contemporaneously with the result of the comparison, or deferred to a later time as desired.

The next phase of a batter's swing may be the forward swing portion of the motion as indicated at 914. In some embodiments, the batter's head motion during the forward swing may be compared with predetermined path data corresponding to head position, at 916, and that the head followed the path of the ball, at 920. In some embodiments, each comparison (e.g., 916 and 920) may be followed by the generation of appropriate feedback (e.g., 918 and 922). Feedback 918 and 922 may be generated contemporaneously with the result of the comparison, deferred to a later time, or combined into one signal as desired.

The next phase of the swing may be impact with the ball as indicated at 924. Some embodiments of the invention may provide a sensor (e.g., a microphone) to record the point of impact with the ball so that the data concurrent with this point may be evaluated.

The next phase of the swing may be follow through as indicated at 926. During this phase, the head gear may compare sensed data with predetermined path data indicating that the head was kept down throughout the follow through motion (e.g., at 928) and that the head remained still for a predetermined time after impact (e.g., 930). Again, feedback 932 may be generated as a result of the comparison. In some embodiments, feedback 932 may be generated if both comparisons (e.g., 928 and 930) result in a noncompliance.

The above descriptions of the golf and baseball embodiments for the head gear are just one example of possible schemes for head motion detection. Of course, other comparison points may be used and other predetermined paths may be stored in the device.

Network Feedback

Figure 13:
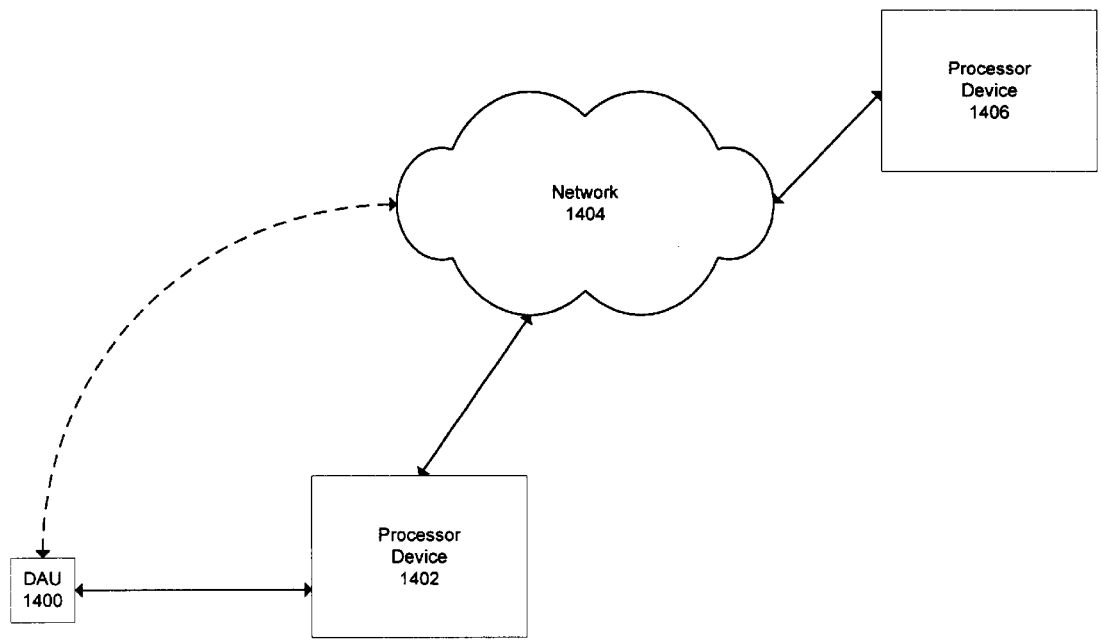
FIG. 13 is a schematic representation of a overall system for providing network feedback according to one embodiment of the invention.

FIG. 13 shows one embodiment of the invention that provides for feedback messages via a network. One embodiment of a method for obtaining feedback over the network may be described with reference to the following example and FIG. 13. In this example embodiment, a user may participate in a physical activity at the user's convenience. For example, the user may play golf on a weekend day. The user operates the head gear while playing golf and stores the head motion data taken during the golf game (e.g., in DAU 1400).

The amount and type of data stored during the game is, of course, variable. For example, the user may store data pertaining only to golf drives, or only to golf putts, or for only the first nine holes, or only for a particular hole, etc.

Once the data is stored, the user may, at the user's convenience, upload the data to a processor device (e.g., processor device 1402). Processor device 1402 may comprise any suitable device for interfacing with a network. For example, processor device 1402 may comprise a PC, laptop, PDA, Web enabled phone, Web enabled TV, or other processor based device.

Processor device may communicate over network 1404 with other processor based devices (e.g., processor 1406). Network 1404 may comprise any network of processor based devices. For example, network 1404 may comprise the Internet, a wide area network (WAN), a local area network (LAN), an intranet, a wireless network, a resort or country club network, or other suitable network.

In some embodiments, DAU 1400 may be enabled to communicate directly over network 1404. For example, DAU 1400 may have a modem (wireless or otherwise) to enable communication over network 1400.

Once connected to network 1404, the stored data relating to the user's head motion may be accessible over the network by other processor devices (e.g. processor 1406). In some embodiments, an evaluator may access the head motion data and provide feedback to the user. An evaluator may be any entity enabled to provide analysis and feedback relating to the head motion data. For example, an evaluator may be a physical activity specialist such as golf professional (e.g., an instructor from Jim McLean's Golf School) or a baseball coach, a person trained to evaluate the head motion data, software or other automated routine that is programmed to evaluate the data, or any other suitable entity.

In some embodiments, the evaluator analyzes the data and generates feedback that is communicated to the user. The communication may take place using any suitable communication channel. For example, the evaluator may send electronic mail (e-mail) to the user, may post comments on a user accessible web page, or any other suitable communication technique.

Figure 14:
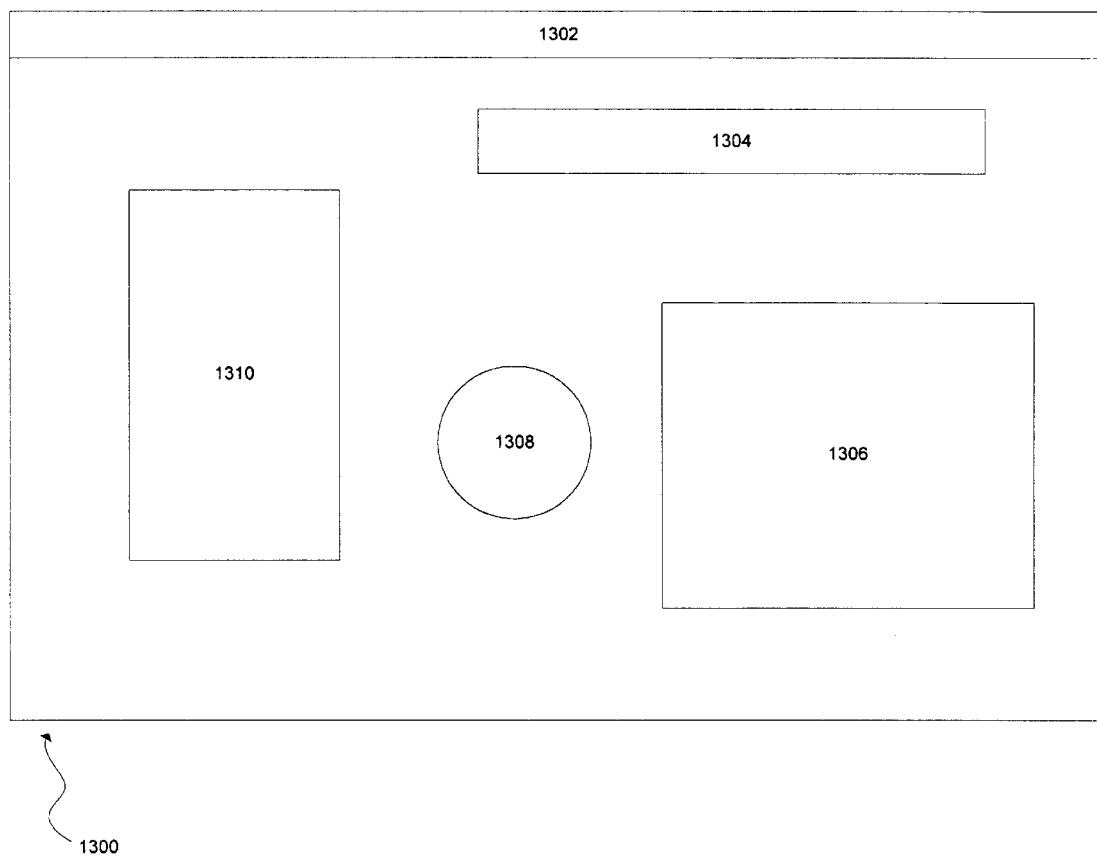
FIG. 14 is a schematic representation of a network site for providing feedback according to one embodiment of the invention.

FIG. 14 is a schematic representation of a network site 1300 for enabling feedback according to one embodiment of the invention. Network site 1300 may comprise any suitable network site (or collection of sites) that enables the uploading of head gear data and generation of feedback. For example, network site 1300 may comprise an Internet web site, or other network site. Network site 1300 may comprise any number of typical site features. For example, site 1300 may comprise features such as: title banner 1302, text hyperlinks 1304, graphical information 1306, advertising 1308, and other site features 1310. In addition, site 1300 may comprise a secure (e.g., password protected) member area, multiple pages, an electronic commerce (e-commerce) shopping area, or other features found on the World Wide Web.

In some embodiments, the user may store several sets of data (e.g., in DAU 1400). The sets of data may then be uploaded to a network site 1300 and evaluated. In some embodiments, network site 1300 may charge a fee to analyze the data. In this manner the user's progress can be tracked over time.

In some embodiments, specific desired head motion paths may be customize to individual users. For example, a collection of the user's head motion data stored over time may be analyzed and processed to generate a personalized best head motion path for that user. In some embodiments, the personalized head motion path may be downloaded to the user and stored (e.g., in DAU 1400). Other system updates, upgrades, revision, or other features may be downloaded to a DAU via a network site 1300 in a similar fashion.

Data Collection Unit

Figure 15:
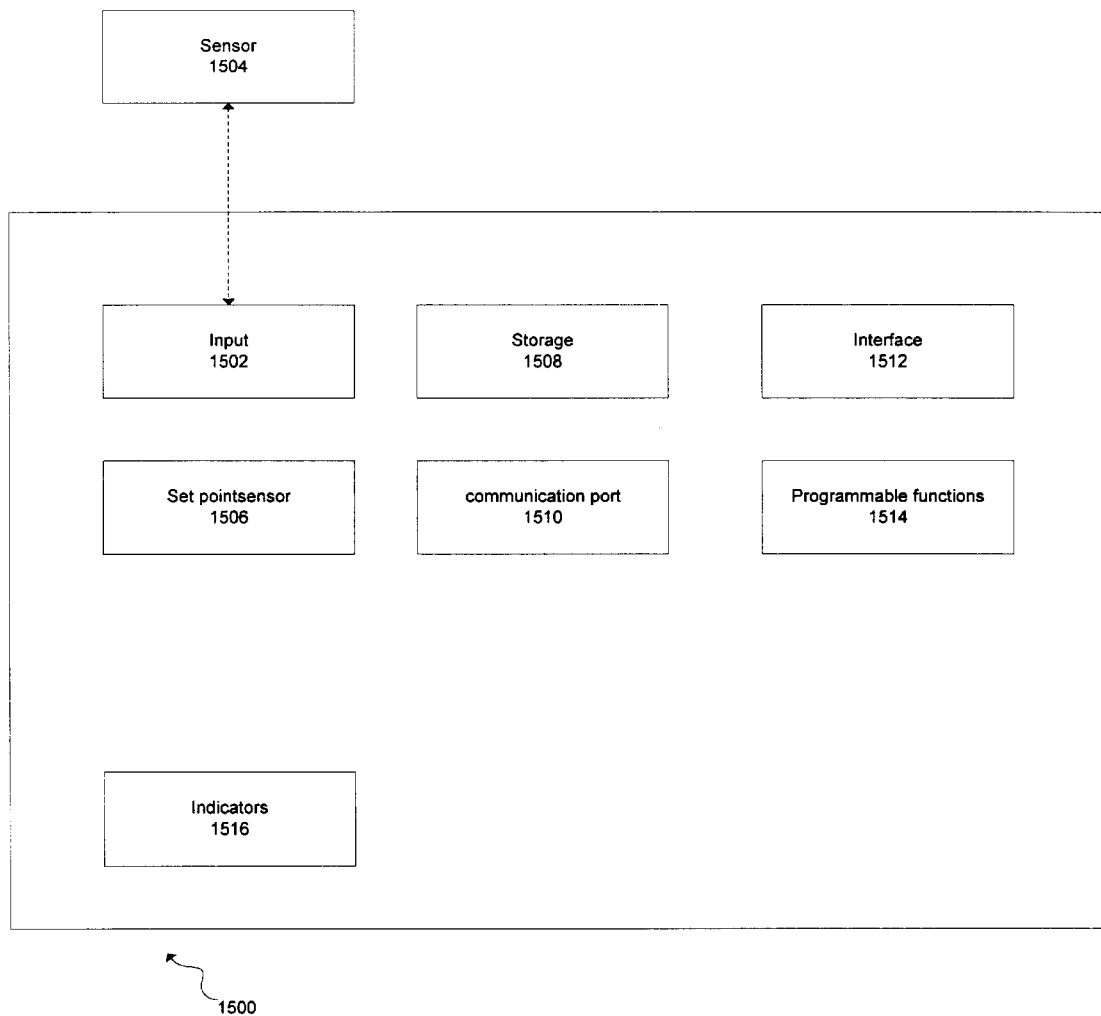
FIG. 15 is a schematic representation of a data collection unit (DCU) according to one embodiment of the invention.

FIG. 15 is a representation of a data collection unit (DCU) according to one embodiment of the invention. In some embodiments, DCU 1500 enables the collection of data used, for example, to create the predetermined path stored in a DAU.

In some embodiments, DCU 1500 may comprise an input channel 1502 for receiving input from a sensor 1504. For example, the DCU may enable the connection of four input devices (e.g., motion sensors) with six channels each for a total of 24 input channels. Of course, more or fewer input channels may be used as desired.

The DCU 1500 may also comprise a sensor 1506 to record the occurrence of a data set point for the motion. For example, sensor 1506 may comprise a microphone to detect audible set points such as the sound of a ball being struck. In some embodiments, the set point may be set manually.

The DCU 1500 may also comprise storage 1508 to store the collected sensor data. The sensor data may be stored in any suitable format. For example, data may be stored in comma separated value (".csv") file formats to facilitate uploading to spread sheet analysis programs. Other formats may be used.

The DCU 1500 may also be enabled for remote operation. For example, DCU 1500 may comprise an communication port 1510 (e.g., modem).

In some embodiments, DCU 1500 may comprise an interface 1512 to enable uploading of stored data to a processor device. For example, DCU 1500 may comprise a RS232 interface for connection to a PC for transfer of data files. Other interfaces are possible.

In some embodiments, the DCU 1500 may comprise a number of programmable functions 1514. For example, DCU 1500 may include programmable buttons for erasing data, clearing memory, arming the input devices, manually designation of set points, snap shot data collection of all input channels, and other functions.

In addition, some embodiments of DCU 1500 may comprise a number of indicators 1516 to communicate operational status and other information pertaining to data collection. For example, DCU 1500 may include audible or visual signal generators to designate events such as, low power, data sample complete, deleted previous sample, erased memory, unit armed, etc.

Other embodiments and uses of the invention will be apparent to those skilled in the art from consideration of the specification and practice of the invention disclosed herein. For example, the head gear may be adapted to other types of athletics not specifically enumerated herein. Athletics may include activities where physical motion occurs and where the monitoring of head position may be useful. The specification and examples should be considered exemplary only. The intended scope of the invention is only limited by the claims appended hereto.

We claim:

1. A method for detecting head motion and providing feedback to a user engaged in a physical activity the method comprising:

providing head gear for wearing on a user's head, wherein the head gear comprises a sensor for detecting motion of the head gear;

providing a processor that
   stores a predetermined head motion value corresponding to a preferred path of motion for the head gear and
   receives input from the sensor indicative of the motion of the head gear;
comparing measured head motion data based on the input from the sensor to the predetermined head motion value; and
generating a feedback signal indicating the result of the comparison;
   wherein the physical activity is a repetitive physical activity; and
   wherein the processor stores predetermined head motion values for a plurality of phases of the repetitive physical activity;
   wherein the step of comparing further comprises comparing the measured head motion data to a stored head motion value indicating that the head gear has remained in an arming position for a predetermined duration.

2. The method of claim 1, wherein the physical activity comprises hitting a golf ball.

3. The method of claim 2, wherein the step of generating a feedback signal further comprises:
   generating an arming feedback signal when the result of the step of comparing indicates that the measured head motion data substantially agrees with the stored head motion value.

4. The method of claim 1, wherein the physical activity comprises hitting a golf ball and the step of comparing further comprises:
   comparing the measured head motion data to a stored head motion value indicating a backswing head position.

5. The method of claim 1, wherein the physical activity comprises hitting a golf ball and the step of comparing further comprises:
   comparing the measured head motion data to a stored head motion value indicating a forward swing head position.

6. The method of claim 1, wherein the physical activity comprises hitting a golf ball and the step of comparing further comprises:
   comparing the measured head motion data to a stored head motion value indicating a follow through head position.

7. The method of claim 1, wherein the physical activity comprises hitting a ball with a bat.

8. The method of claim 7, wherein the step of generating a feedback signal further comprises:
   generating a first arming feedback signal when the result of the step of comparing indicates that the input substantially agrees with the stored head motion value; and
   generating a second arming feedback signal when the result of the step of comparing indicates that the input does not substantially agree with the stored head motion value.

9. The method of claim 1, wherein the physical activity comprises hitting a ball with a bat and the step of comparing further comprises:
   comparing the measured head motion data to a stored head motion value indicating a load at pitch head position.

10. The method of claim 9, wherein the step of generating a feedback signal further comprises:
   generating a load at pitch feedback signal when the result of the step of comparing indicates that the measured head motion value deviates from the stored head motion value.

11. The method of claim 1, wherein the physical activity comprises hitting a ball with a bat and the step of comparing further comprises:
   comparing the measured head motion data to a stored head motion value indicating bat swing head position.

12. The method of claim 11, wherein the step of generating a feedback signal further comprises:
   generating a feedback signal when the result of the step of comparing indicates that the measured head motion data deviates from the stored head motion value.

13. The method of claim 1, wherein the physical activity comprises hitting a ball with a bat and the step of comparing further comprises:
   comparing the measured head motion data to a stored head motion value indicating follow through head position.

14. The method of claim 13, wherein the step of generating a feedback signal further comprises:
   generating a feedback signal when the result of the step of comparing indicates that the measured head motion data deviates from the stored head motion value.

15. An apparatus for detecting the motion of a user's head during the user's performance of a physical activity, the apparatus comprising:
   a sensor, wearable on the user's head, wherein the sensor detects motion of the user's head;
   a processor that
      stores a predetermined head motion value corresponding to a preferred path of motion for the head gear,
      receives input from the sensor indicative of the motion of the head gear, and
      compares measured head motion data based on the input from the sensor to the stored head motion value; and
   a feedback indicator that generates a feedback signal indicative of the result of the comparison; and
      wherein the physical activity is a repetitive physical activity; and
      wherein the processor stores predetermined head motion values for a plurality of phases of the repetitive physical activity;
      wherein the comparison by the processor further comprises comparing the measured head motion data to a stored head motion value indicating that the apparatus has remained in an arming position for a predetermined duration.

16. The apparatus of claim 15, wherein the sensor further comprises:
   a band, wearable about the user's head, and comprising at least three sensor nodes positioned around the band.

17. The apparatus of claim 16, wherein the at least three sensor nodes are positioned around the band at positions along a circumference of the band that substantially correspond to locations of about 90 degrees, 180 degrees, and 270 degrees.

18. The apparatus of claim 15, wherein the sensor comprises a gyroscopic sensor.

19. The apparatus of claim 15, wherein the sensor comprises an accelerometer sensor.

20. The apparatus of claim 15, wherein the processor further comprises:
   a data augmentation unit comprising a first portable processor based device.

21. The apparatus of claim 20, wherein the data augmentation unit further comprises:

an interface that enables data stored in the data augmentation device to be uploaded to a second processor based device.

22. The apparatus of claim 20, wherein the data augmentation unit further comprises:

a user interface to enable the user to input information.

23. The apparatus of claim 21, wherein at least one of the first and second processor based devices is capable of communicating over the Internet.

24. The apparatus of claim 22, wherein the input information further comprises:

information relating to a club type or swing type.

25. The apparatus of claim 22, wherein the input information further comprises:

information relating to a distance from a target.

26. The apparatus of claim 22, wherein the input information further comprises:

information relating to an angle from a target.

27. The apparatus of claim 22, wherein the input information further comprises:

information relating to scorekeeping.

28. The apparatus of claim 22, wherein the input information further comprises:

information relating to a pitch type.

29. The apparatus of claim 22, wherein the input information further comprises:

information relating to a pitch speed.

30. The apparatus of claim 22, wherein the input information further comprises:

information relating to a pitch location.

31. The apparatus of claim 22, wherein the input information further comprises:

information relating to a hit result.

32. The apparatus of claim 22, wherein the input information further comprises:

information relating to a field position.

33. The apparatus of claim 22, wherein the input information further comprises:

information relating to a batting average.

34. The apparatus of claim 20, wherein the data augmentation unit receives input from the sensor via a wireless connection.

35. The apparatus of claim 15, wherein the feedback indicator further comprises:

a display.

36. The apparatus of claim 35, wherein the display further comprises:

a screen for displaying visually perceptible information.

37. A method of evaluating a physical activity by processing head motion data, comprising:

providing a head device including sensors for sensing head motion during a repetitive type of physical activity;

providing a processor device including stored predetermined values corresponding to preferred head motion, the stored predetermined values corresponding to a plurality of identified phases of the physical activity;

wearing said head device during the physical activity;

receiving input data from said sensors corresponding to head motion during the physical activity;

processing the input data according to the stored predetermined values to generate a feedback signal;

wherein the feedback signal represents at least one of a positive and a negative feedback for one or more of said plurality of identified phases;

wherein the step of processing further comprises comparing measured head motion data to a stored head motion value indicating that the head device has remained in an arming position for a predetermined duration.

38. The method of claim 37, wherein the physical activity is a golf swing and the phases include a backswing and a forward swing.

39. The method of claim 38, wherein the phases further include an address position.

40. The method of claim 38, wherein the phases further include a follow-through.

41. The method of claim 38, further comprising the step of receiving a user input of a club type or a swing type.

42. The method of claim 40, wherein the phases further include an impact phase.

43. The method of claim 37, wherein the physical activity is a baseball swing and the phases include a forward swing and a follow-through.

44. The method of claim 43, wherein the phases further include a batting stance position.

45. The method of claim 43, wherein the phases further include a load pitch phase.

46. The method of claim 43, wherein the phases further include an impact phase.

47. A method for detecting head motion and providing feedback to a user engaged in a physical activity the method comprising:

providing head gear for wearing on a user's head, wherein the head gear comprises a sensor for detecting motion of the head gear;

providing a processor that
stores a predetermined head motion value corresponding to a preferred path of motion for the head gear and
receives input from the sensor indicative of the motion of the head gear;

comparing measured head motion data based on the input from the sensor to the predetermined head motion value; and generating a feedback signal indicating the result of the comparison;

wherein the physical activity is a repetitive physical activity; and wherein the processor stores predetermined head motion values for a plurality of phases of the repetitive physical activity;

wherein the physical activity comprises hitting a golf ball and the step of comparing further comprises comparing the measured head motion data to a stored head motion value indicating a backswing head position;

wherein the step of generating a feedback signal further comprises:
generating a first backswing feedback signal when the result of the step of comparing indicates that the head gear rotated beyond a predetermined rotation point;
generating a second backswing feedback signal when the result of the step of comparing indicates that the head gear translated beyond a predetermined translation point; and
generating a third backswing feedback signal when the result of the step of comparing indicates that the head gear inclined or declined beyond a predetermined inclination point.

48. A method for detecting head motion and providing feedback to a user engaged in a physical activity the method comprising:

provscriptsing head gear for wearing on a user's head, wherein the head gear comprises a sensor for detecting motion of the head gear;

providing a processor that
stores a predetermined head motion value corresponding to a preferred path of motion for the head gear and
receives input from the sensor indicative of the motion of the head gear;

comparing measured head motion data based on the input from the sensor to the predetermined head motion value; and generating a feedback signal indicating the result of the comparison;

wherein the physical activity is a repetitive physical activity; and wherein the processor stores predetermined head motion values for a plurality of phases of the repetitive physical activity;

wherein the physical activity comprises hitting a golf ball and the step of comparing further comprises comparing the measured head motion data to a stored head motion value indicating a forward swing head position;

wherein the step of generating a feedback signal further comprises:
generating a first forward swing feedback signal when the result of the step of comparing indicates that the head gear rotated beyond a predetermined rotation point;
generating a second forward swing feedback signal when the result of the step of comparing indicates that the head gear translated beyond a predetermined translation point; and
generating a third forward swing feedback signal when the result of the step of comparing indicates that the head gear inclined or declined beyond a predetermined inclination point.

49. A method for detecting head motion and providing feedback to a user engaged in a physical activity the method comprising:

providing head gear for wearing on a user's head, wherein the head gear comprises a sensor for detecting motion of the head gear;

providing a processor that
stores a predetermined head motion value corresponding to a preferred path of motion for the head gear and
receives input from the sensor indicative of the motion of the head gear;

comparing measured head motion data based on the input from the sensor to the predetermined head motion value; and generating a feedback signal indicating the result of the comparison;

wherein the physical activity is a repetitive physical activity; and wherein the processor stores predetermined head motion values for a plurality of phases of the repetitive physical activity;

wherein the physical activity comprises hitting a golf ball and the step of comparing further comprises comparing the measured head motion data to a stored head motion value indicating a follow through head position;

wherein the step of generating a feedback signal further comprises:
generating a first follow through feedback signal when the result of the step of comparing indicates that the head gear rotated beyond a predetermined rotation point;
generating a second follow through feedback signal when the result of the step of comparing indicates that the head gear translated beyond a predetermined translation point; and
generating a third follow through feedback signal when the result of the step of comparing indicates that the head gear inclined or declined beyond a predetermined inclination point.

* * * * *